US009891199B2

(12) United States Patent
Sasano

(10) Patent No.: US 9,891,199 B2
(45) Date of Patent: Feb. 13, 2018

(54) PRE-ANALYSIS TREATMENT DEVICE USABLE FOR AMINO ACID, ORGANIC ACID, AND GLUCIDE AND PRE-ANALYSIS TREATMENT METHOD

(71) Applicant: AiSTI SCIENCE CO., Ltd., Wakayama-shi (JP)

(72) Inventor: Ryoichi Sasano, Wakayama (JP)

(73) Assignee: AISTI SCIENCE CO., LTD., Wakayama-shi (JP)

( * ) Notice: Subject to any disclaimer, the term of this patent is extended or adjusted under 35 U.S.C. 154(b) by 0 days.

(21) Appl. No.: 15/502,877

(22) PCT Filed: Aug. 10, 2015

(86) PCT No.: PCT/JP2015/072703
§ 371 (c)(1),
(2) Date: Feb. 9, 2017

(87) PCT Pub. No.: WO2016/024575
PCT Pub. Date: Feb. 18, 2016

(65) Prior Publication Data
US 2017/0234843 A1    Aug. 17, 2017

(30) Foreign Application Priority Data

Aug. 12, 2014  (JP) ................................ 2014-164554
Mar. 4, 2015   (JP) ................................ 2015-042999

(51) Int. Cl.
*G01N 30/96*  (2006.01)
*G01N 1/40*   (2006.01)
(Continued)

(52) U.S. Cl.
CPC ............. *G01N 30/96* (2013.01); *G01N 1/405* (2013.01); *G01N 30/84* (2013.01); *G01N 30/88* (2013.01);
(Continued)

(58) Field of Classification Search
CPC ........... G01N 1/405; G01N 2030/8435; G01N 2030/8804; G01N 2030/884;
(Continued)

(56) References Cited

U.S. PATENT DOCUMENTS 6,260,407 B1 *   7/2001   Petro ..................... B01D 15/08
                                                          210/198.2
9,625,429 B2 *   4/2017   Herman ............. G01N 30/7233
(Continued)

FOREIGN PATENT DOCUMENTS

JP    H09-329589    12/1997
JP    2000-310626   11/2000
JP    4780109 B2    9/2011

OTHER PUBLICATIONS

International Search Report for International Application No. PCT/JP2015/072703 dated Dec. 8, 2015.

*Primary Examiner* — Samuel P Siefke
(74) *Attorney, Agent, or Firm* — Kratz, Quintos & Hanson, LLP

(57) ABSTRACT

A pre-analysis treatment device usable for an amino acid, organic acid, and glucide includes an ion-exchange unit configured to load a test sample on a solid-phase cartridge S having a strong ion-exchange resin phase, to allow the strong ion-exchange resin phase to adsorb a predetermined organic compound, then supply a dehydration solvent to dehydrate the strong ion-exchange resin phase, and a derivatization unit configured to feed a predetermined amount of the derivatization reagent to the dehydrated strong ion-exchange resin phase to allow the derivatization reagent to retain for a predetermined time period, thereby trimethylsilylating the organic compound adsorbed on the strong ion-exchange resin phase, and simultaneously desorbing the trimethylsilylated organic compound from the strong ion-exchange resin phase, and then supply a push-out solvent to (Continued)

push the trimethylsilylated organic compound desorbed, out of the solid-phase cartridge S. The device enables at least one organic compound selected from amino acids, organic acids and glucides contained in a test sample to be derivatized and collected easily in a short period of time, and automation of the pre-analysis treatment.

12 Claims, 11 Drawing Sheets

(51) Int. Cl.
*G01N 30/84* (2006.01)
*G01N 30/88* (2006.01)
*G01N 35/10* (2006.01)

(52) U.S. Cl.
CPC ..... *G01N 35/1004* (2013.01); *G01N 35/1095* (2013.01); *G01N 2030/8435* (2013.01); *G01N 2030/8804* (2013.01); *G01N 2030/884* (2013.01); *G01N 2035/1053* (2013.01)

(58) Field of Classification Search
CPC ........... G01N 2035/1053; G01N 30/84; G01N 30/88; G01N 30/96; G01N 35/1004; G01N 35/1095
See application file for complete search history.

(56) References Cited

U.S. PATENT DOCUMENTS

| 2004/0223880 | A1* | 11/2004 | Gjerde | G01N 1/34 422/70 |
| 2008/0093300 | A1* | 4/2008 | Clarke | B01D 15/1864 210/656 |
| 2010/0237235 | A1* | 9/2010 | Ozbal | G01N 30/24 250/282 |
| 2014/0251911 | A1* | 9/2014 | Skudas | B01D 15/1864 210/656 |
| 2015/0089997 | A1* | 4/2015 | Nema | G01N 30/52 73/23.4 |

* cited by examiner

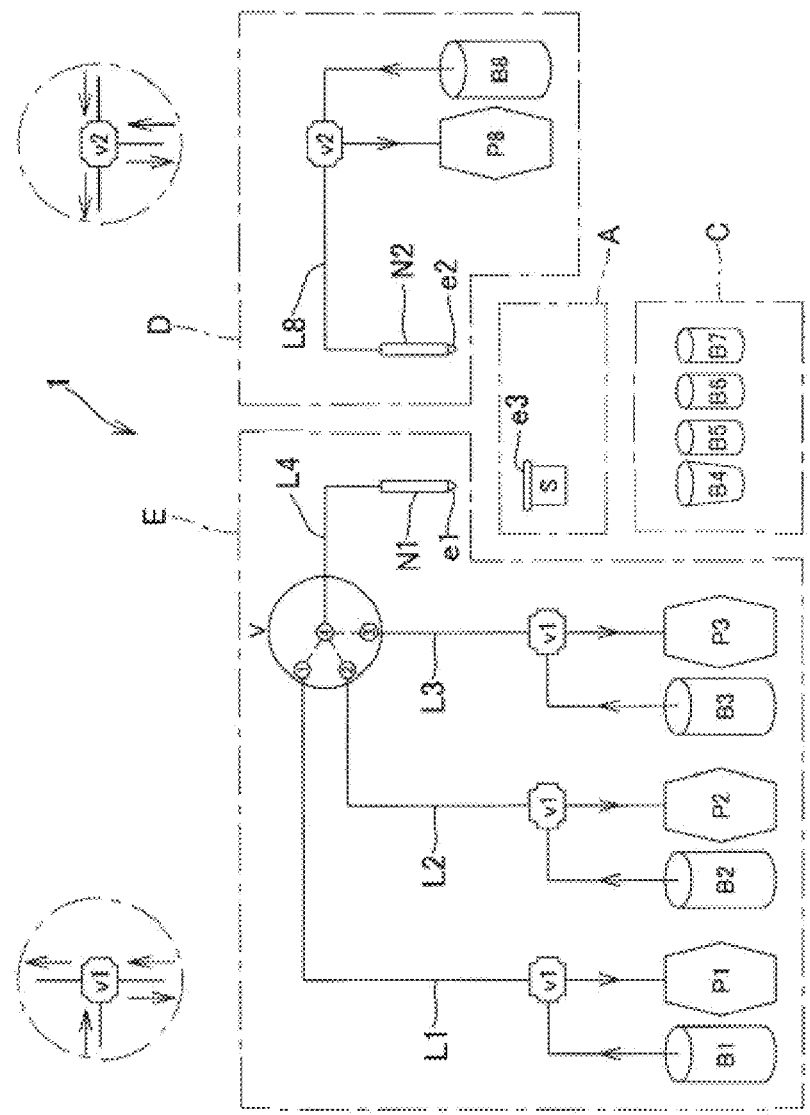
[Fig. 1]

[Fig. 2]
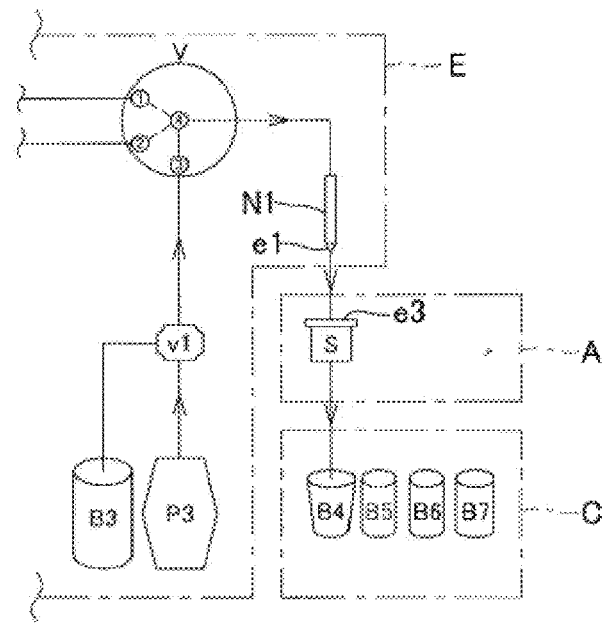
[Fig. 3]
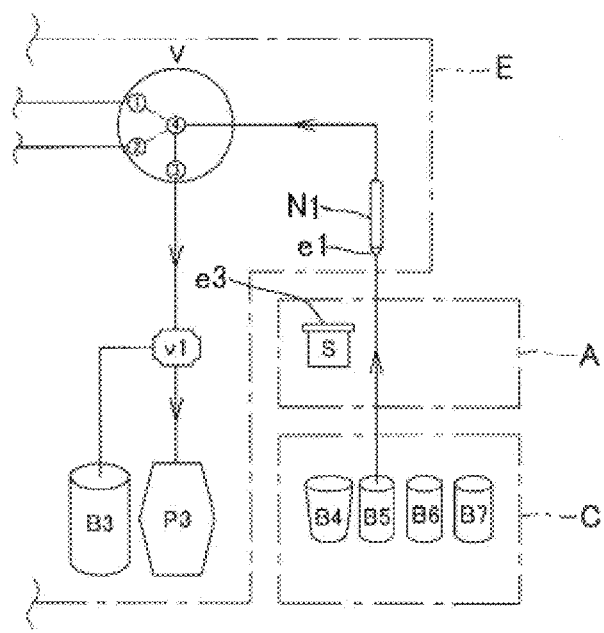

[Fig. 4]
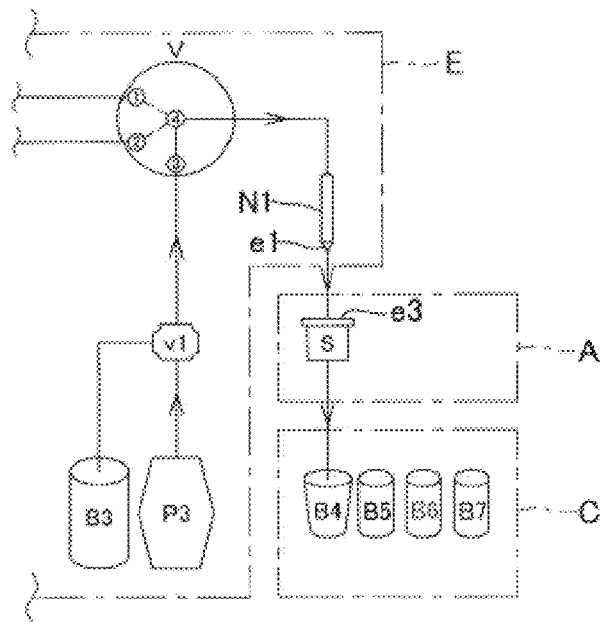
[Fig. 5]
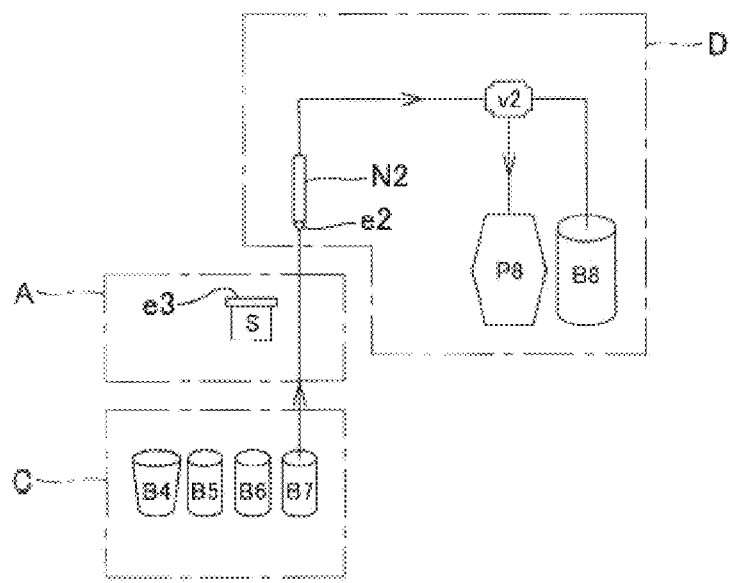

[Fig. 6]
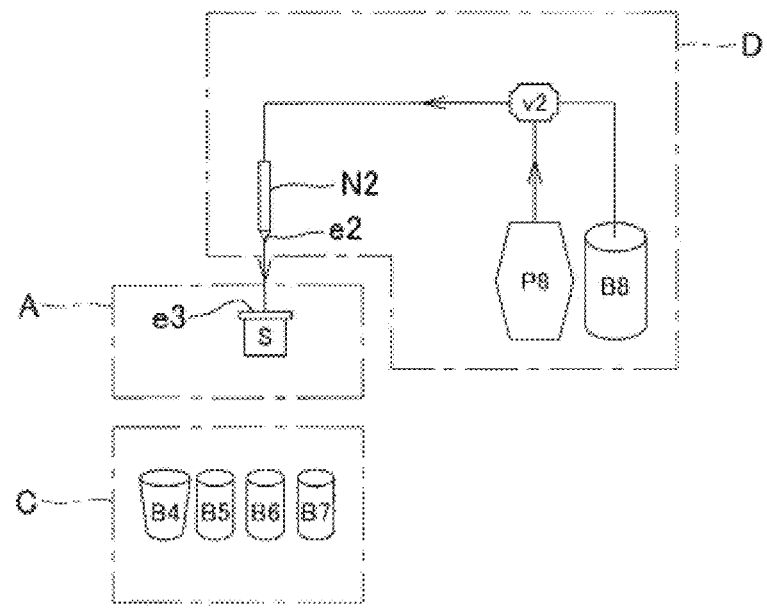
[Fig. 7]
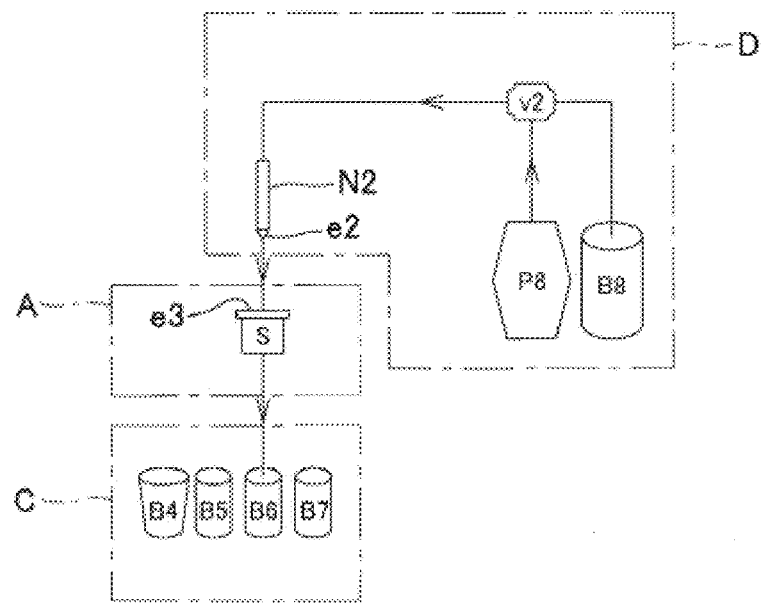

[Fig. 8]
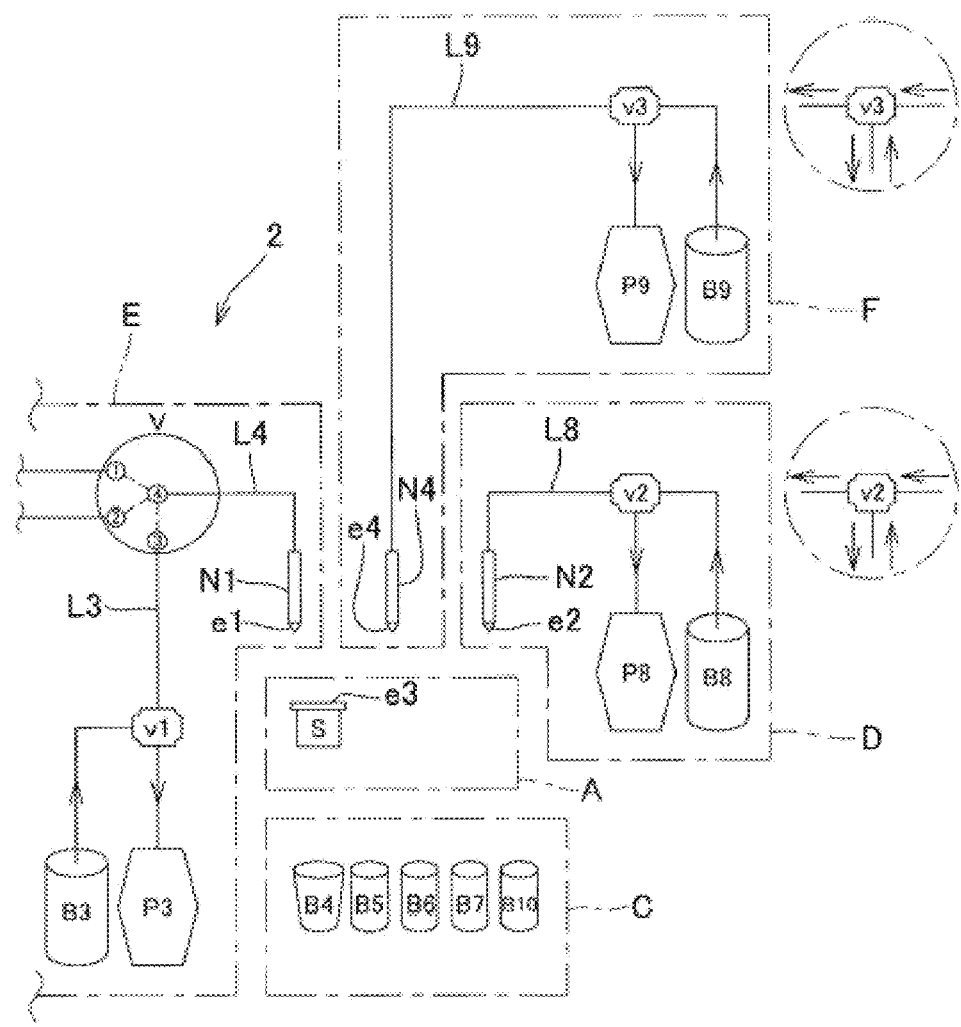

[Fig. 9]
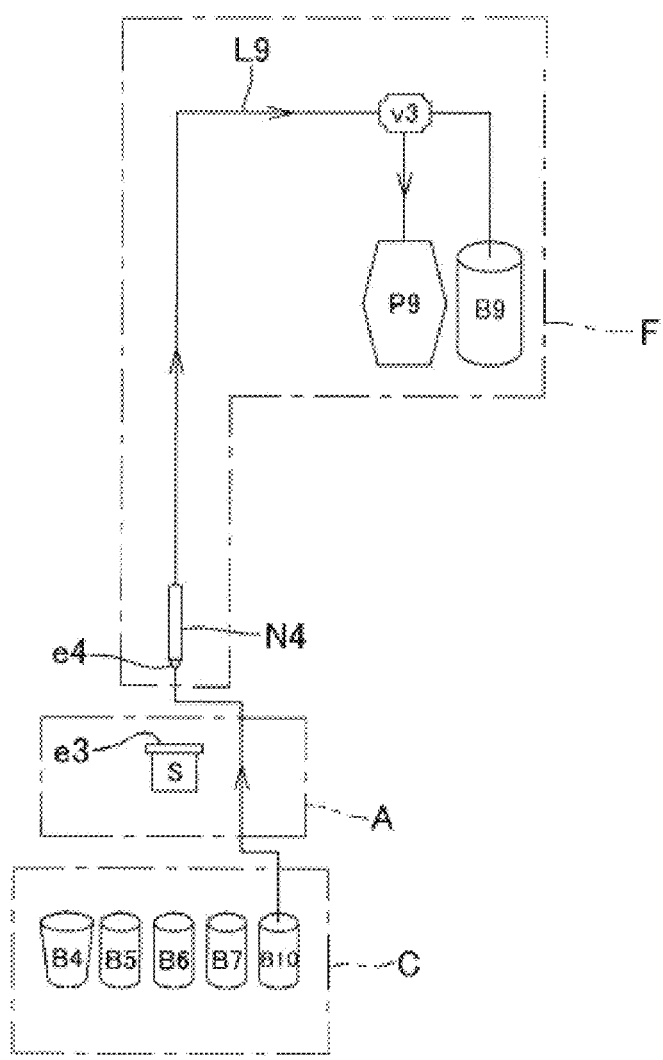

[Fig. 10]
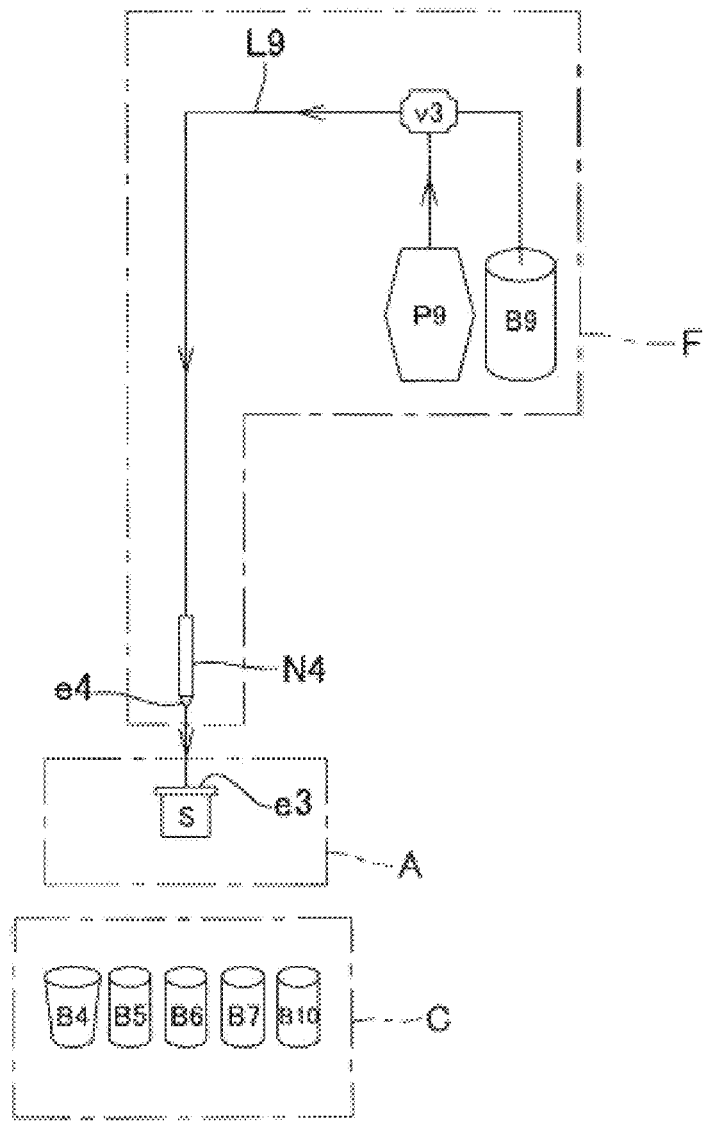

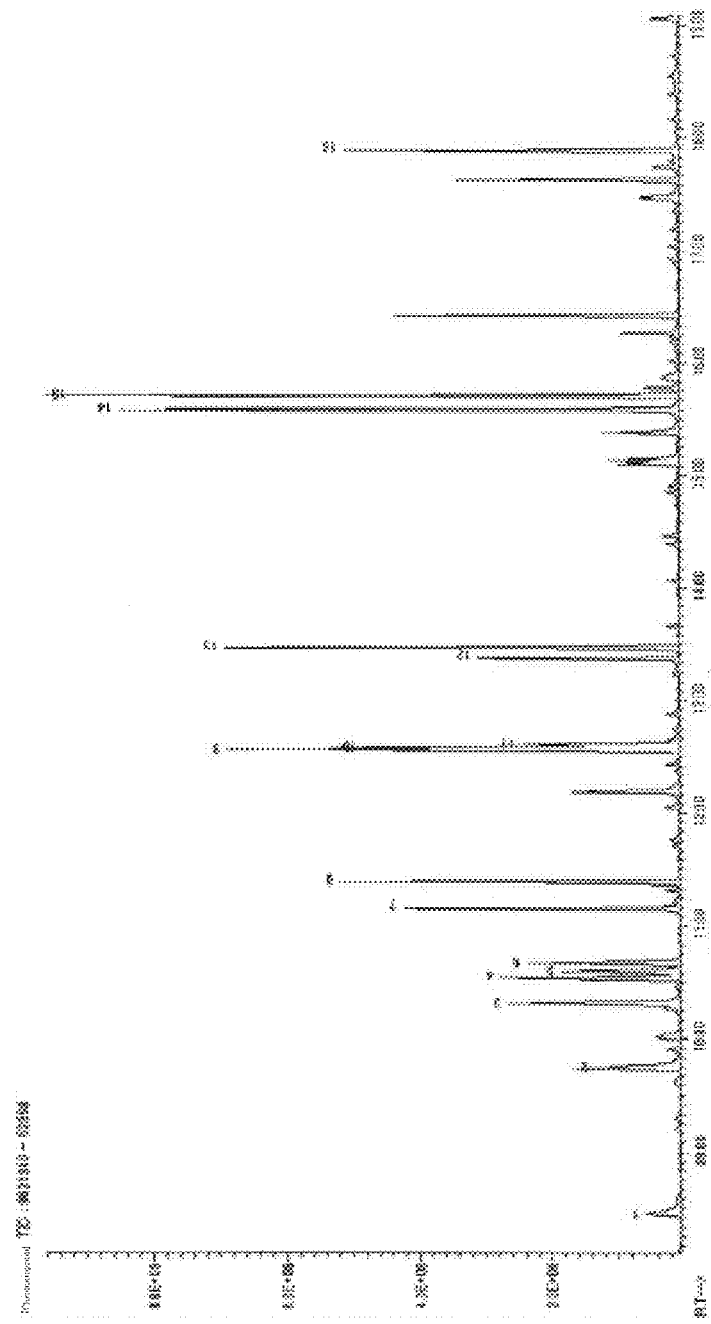
[Fig. 11]

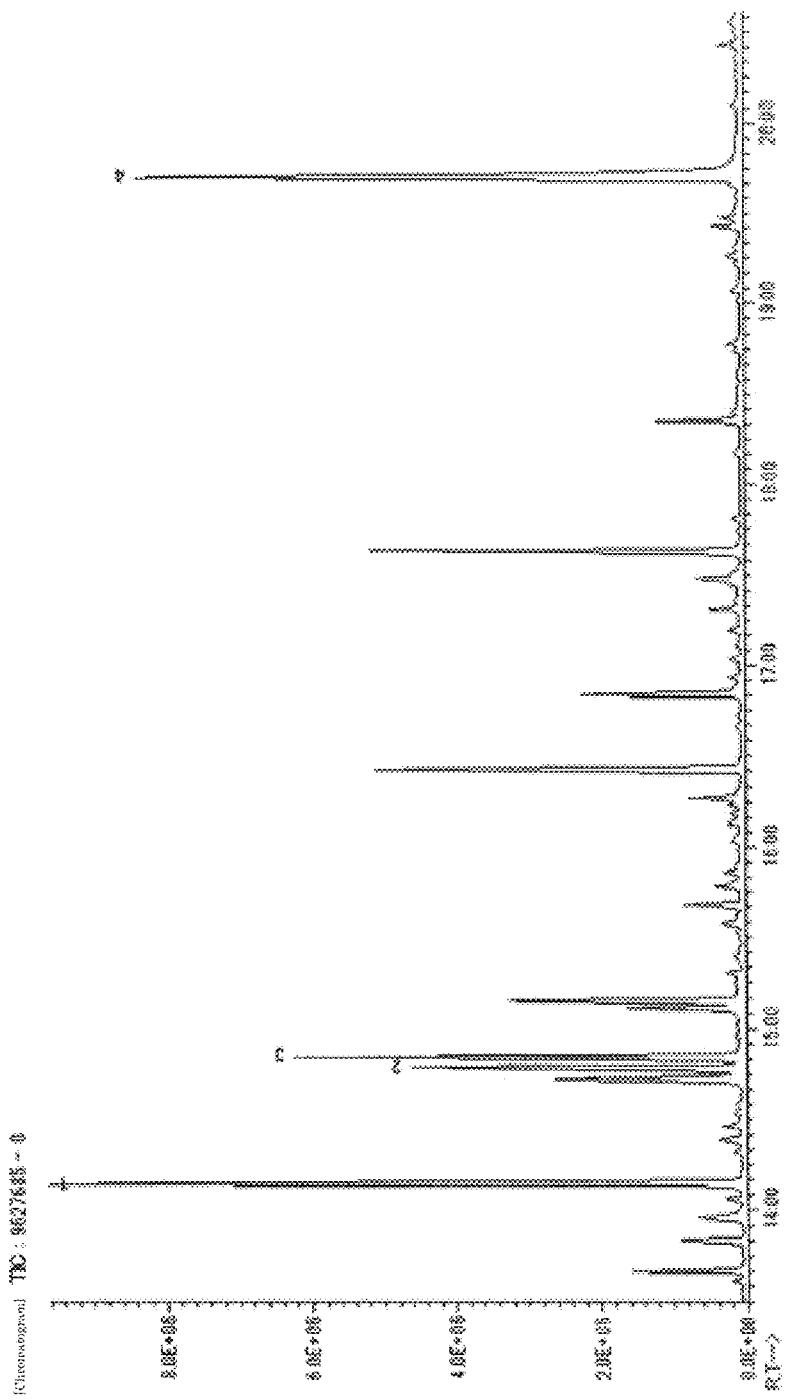
[Fig. 12]

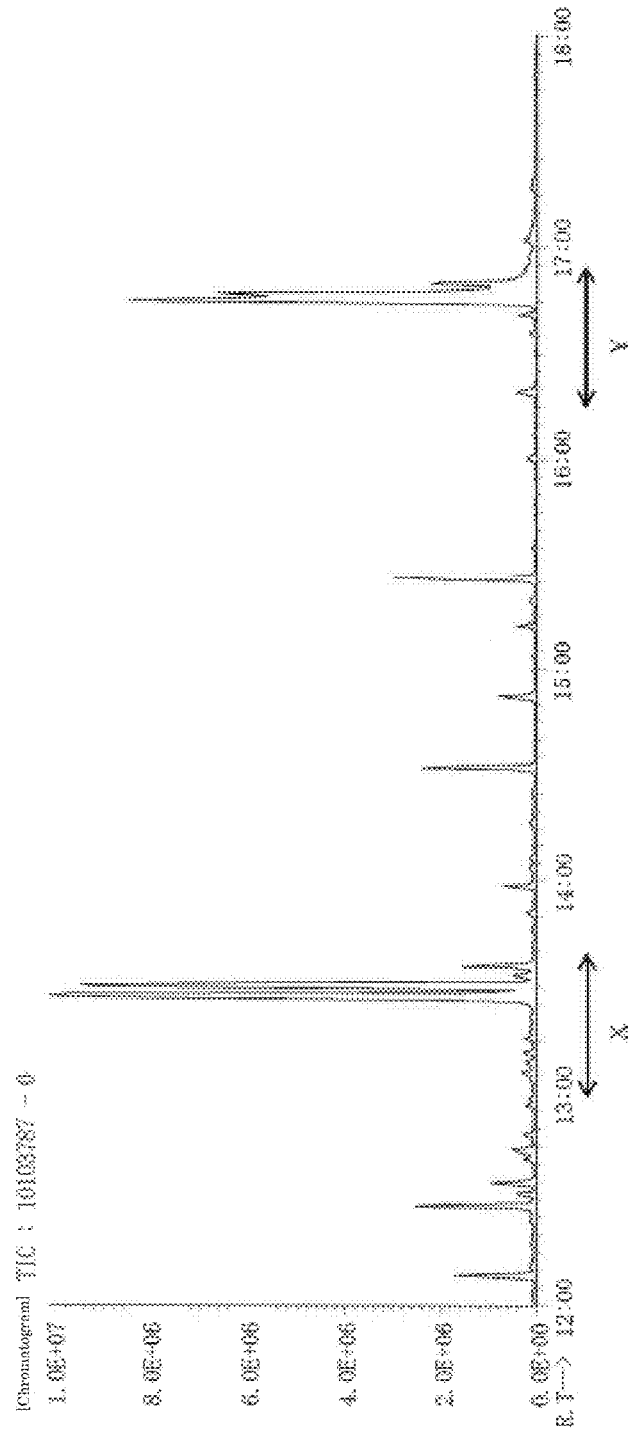
[Fig. 13]

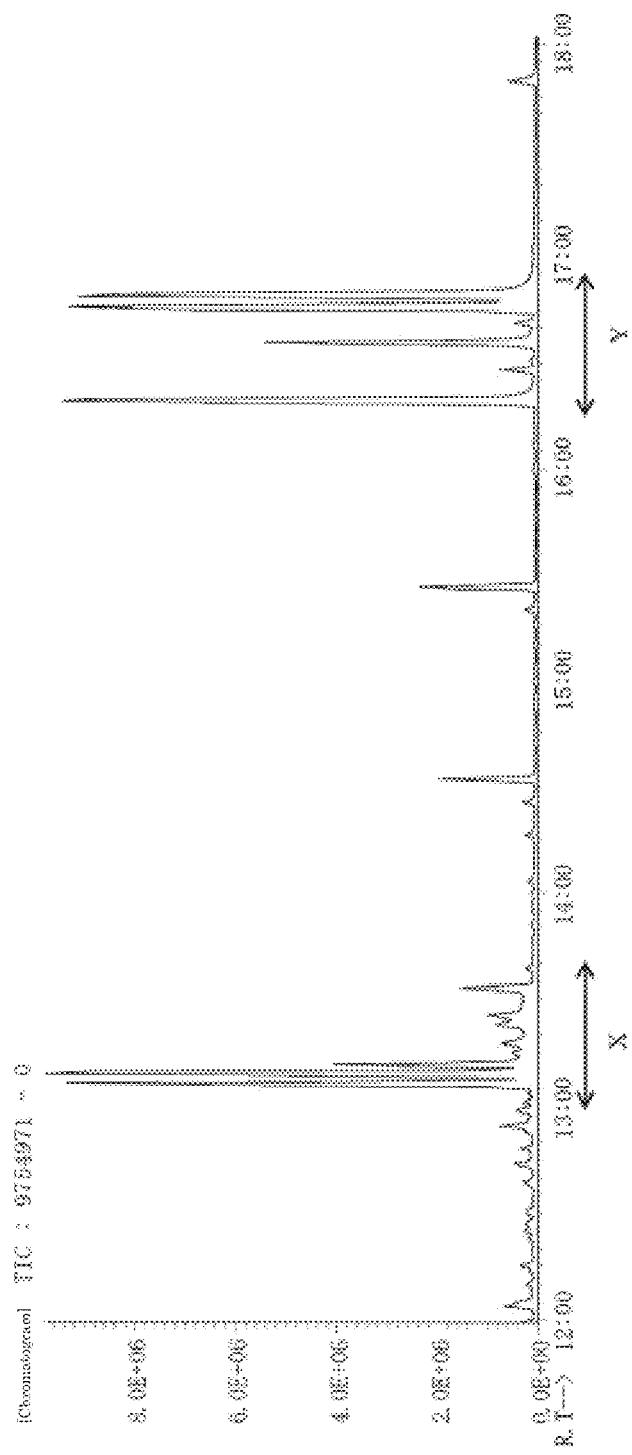
[Fig. 14]

PRE-ANALYSIS TREATMENT DEVICE USABLE FOR AMINO ACID, ORGANIC ACID, AND GLUCIDE AND PRE-ANALYSIS TREATMENT METHOD

TECHNICAL FIELD

The present invention relates to a pre-analysis treatment device usable for amino acid, organic acid and glucide and a pre-analysis treatment method and, in particular, to a pre-analysis treatment device and a pre-analysis treatment method for quantitative analysis of amino acids, organic acids and glucides contained in test sample.

BACKGROUND ART

Recently, an analytical method for studying apparently invisible biological phenomena by determining metabolites contained in organisms comprehensively and quantitatively is attracting attentions. The analytical method, which is also called metabolome analysis, is attempted to be applied to the medical field, for example in disease diagnosis and etiological analysis, and also to the pharmaceutical field, for example in analysis of toxicity or adverse reaction. In addition to the medical and pharmaceutical fields, the analytical method is expected to be applied to other fields, for example for food quality control, quality rating, quality prediction, food stability evaluation, optimization of food production and breeding of industrial microbes, plants and others.

As described above in the metabolome analysis, there exists a need for conducting a quantitative analysis for quantitative determination of the substances to be analyzed. A gas chromatography mass spectrometer or a liquid chromatography mass spectrometer is generally used as such an instrument for quantitative analysis. However, substances to be analyzed such as biological metabolites are highly water-soluble low-molecular weight compounds such as amino acids, organic acids, and glucides, so that these compounds need to be derivatized for analysis on these analyzers. Thus, for comprehensive and quantitative analysis of analyte substances contained in the test sample, it is needed first to obtain many analyte substances from a collected test sample comprehensively, derivatize these substances and thus prepare a test sample solution suited for these analyzers.

Traditionally, for preparation of such a test sample solution, a sample was dried for complete removal of water; the dried sample was mixed with a prescribed substance sufficiently and heated for 60 to 90 minutes for modification of the carbonyl, amino, and hydroxyl groups of amino acids and glucides; further, a derivatization reagent was added thereto and the mixture was agitated sufficiently and heated for 30 to 60 minutes; and the resulting solution was analyzed within 24 hours after its preparation. In this way, there were needed a significant period of time and much labor for preparation of a test sample for metabolome analysis, and thus metabolome analysis was limited in applicability, although its usefulness was attracting attentions.

As a method to overcome the problem above, Patent Document 1 discloses a kit employing a pipette that can make free amino acids contained in sample be adsorbed on an ion-exchange resin by treatment of a test sample with the ion-exchange resin, elute the amino acids therefrom with an ion-exchanging elution medium, i.e., water or an aqueous salt solution, and derivatize (alkylate or esterify) the free amino acids contained in the eluate. It is also described that the free amino acids are eluted with an elution medium, liberated and alkylated or esterified in the presence of the elution medium and the ion-exchange resin, if it is a styrene-divinylbenzene copolymer-based ion-exchange resin.

Alternatively, Patent Document 2 discloses a pre-analysis treatment device that can separate analyte substances from a test sample so as to obtain a test sample solution.

However, although Patent Document 1 discloses a kit employing the pipette, it does not disclose a device that can be automated to collect the derivatized amino acids. In addition, derivatization of amino acids described therein was alkylation or esterification and there was no description on trimethylsilylation. Although separation of some analyte substances such as residual agricultural chemicals and environmental hormones, contained in the test sample was described in Patent Document 2, there was no description on derivatization of the analyte substances for subsequent analysis or on the instrument and the method that can give derivatized amino acids, organic acids and glucides.

CITATION LIST

Patent Literature

Patent Document 1: JP-A No. 2000-310626
Patent Document 2: JP No. 4780109

SUMMARY OF THE INVENTION

Technical Problem

As described above, Patent Documents 1 and 2 do not disclose any automatable pre-analysis treatment device or method that selects amino acids, organic acids and glucides in a test sample and collects these organic compounds after derivatization by trimethylsilylation. Also in the method described in Patent Document 1, for example in operation for alkylation or esterification of amino acids, amino acids are derivatized in the presence of a water-containing elution medium, a derivatization reagent (non-aqueous solvent) and, as needed, an ion-exchange resin, and the derivatized amino acids are extracted into organic layer. First before the derivatization, the free amino acids adsorbed are eluted from the ion-exchange resin by ion exchange interaction, using an aqueous salt solution as the elution medium. However, when amino acids are trimethylsilylated, the derivatization becomes unstable in the presence of water, and water should be removed completely before derivatization. It is thus unfavorable to use the method described in Patent Document 1 to reliably derivatize amino acids by trimethylsilylation. In addition, as described in Patent Document 1, in the case of an ion-exchange resin based on styrene-divinylbenzene copolymer, it is needed to collect the derivatized amino acids extracted into organic layer, from mixture of the derivatized amino acids, the elution medium, the derivatization reagent, and the ion-exchange resin, causing the complicated operation. Thus, it is difficult to automate the procedure.

On the other hand, for comprehensive and quantitative analysis of test sample, as in metabolome analysis, needed are a pre-analysis treatment device and a pre-analysis treatment method that can perform quantitative analysis of a collected test sample easily in a short period of time and is also readily automatable, and there exists a demand for development of such a device or method.

Thus, an object of the present invention is to provide a pre-analysis treatment device and a pre-analysis treatment method that can derivatize and collect at least one organic compound selected from amino acids, organic acids, and glucides contained in test sample easily in a short period of time, and that is also automatable.

Solution to Problem

After intensive studies to solve the problems above, the inventor have found that it is possible to solve the problems above by ion-exchanging a test sample by using a solid-phase cartridge containing a particular ion-exchange resin phase as the solid-phase cartridge that adsorbs at least one organic compound selected from amino acids, organic acids, and glucides, derivatizing the organic compound adsorbed on the ion-exchange resin phase, in a particular manner, simultaneously desorbing the derivatized organic compounds from the ion-exchange resin phase, and then push out and collecting the trimethylsilylated organic compound with a particular push-out solvent (i.e., elution solvent). The inventor thus made the present invention. Summary of the present invention is as follows:

(1) A pre-analysis treatment device usable for an amino acid, organic acid, and glucide, the pre-analysis treatment device includes
a sample-storing unit for storing a test sample,
a solid-phase cartridge having a strong ion-exchange resin phase that adsorbs at least one organic compound selected from amino acids, organic acids and glucides possibly contained in the test sample,
a dehydration solvent-storing unit for storing a dehydration solvent that dehydrates the strong ion-exchange resin phase on which the test sample is loaded,
a first nozzle used for at least one of discharging the dehydration solvent, withdrawing the test sample, and ejecting the test sample,
a first feed pump for supplying the dehydration solvent and the test sample via the first nozzle to the solid-phase cartridge,
a derivatization reagent-storing unit for storing a derivatization reagent that trimethylsilylates the organic compound adsorbed on the strong ion-exchange resin phase,
a push-out solvent-storing unit for storing a non-ion-exchanging push-out solvent that pushes the trimethylsilylated organic compound out of the solid-phase cartridge,
a second nozzle used for at least one of discharging the elution solvent, withdrawing the derivatization reagent, and discharging the derivatization reagent,
a second feed pump for supplying the derivatization reagent and the elution solvent via the second nozzle to the solid-phase cartridge,
an ion-exchange unit configured to (i) withdraw a prescribed amount of the test sample by the first feed pump in a state that an outlet side of the first nozzle is connected to the sample-storing unit, (ii) then feed the test sample withdrawn, with the dehydration solvent in a state that the outlet side of the first nozzle is connected to an inlet side of the solid-phase cartridge, (iii) load the test sample on the solid-phase cartridge to allow the strong ion-exchange resin phase to adsorb the organic compound, and (iv) then supply the dehydration solvent to dehydrate the strong ion-exchange resin phase, and
a derivatization unit configured to (i) withdraw a prescribed amount of derivatization reagent by the second feed pump in a state that an outlet side of the second nozzle is connected to the derivatization reagent-storing unit, (ii) feed the prescribed amount of the derivatization reagent with the elution solvent in a state that the outlet side of the second nozzle is connected to an inlet side of the solid-phase cartridge, (iii) suspend the feed of the elution solvent for a particular time so as to retain the derivatization reagent, thereby trimethylsilylating the organic compound adsorbed on the strong ion-exchange resin phase in the ion-exchange unit, and simultaneously desorbing the trimethylsilylated organic compound from the strong ion-exchange resin phase, and (iv) then supply the push-out solvent to push the desorbed trimethylsilylated organic compound out of the solid-phase cartridge.

(2) The pre-analysis treatment device usable for an amino acid, organic acid, and glucide described above in (1), further includes
a pretreatment reagent-storing unit for storing a trimethylsilylation pretreatment reagent for generating a particular isomer of an organic compound preferentially among multiple isomers possibly generated during trimethylsilylation,
a third nozzle for withdrawing or ejecting the trimethylsilylation pretreatment reagent,
a third pump for supplying the trimethylsilylation pretreatment reagent via the third nozzle to the solid-phase cartridge, and a trimethylsilylation pretreatment unit configured to (i) withdraw a prescribed amount of the trimethylsilylation pretreatment reagent by the third feed pump in a state that the outlet side of the third nozzle is connected to the pretreatment reagent-storing unit, (ii) feed the prescribed amount of the trimethylsilylation pretreatment reagent in a state that the outlet side of the third nozzle is connected to the inlet side of the solid-phase cartridge, and (iii) suspend the feed of the trimethylsilylation pretreatment reagent for a particular time, thereby retaining the trimethylsilylation pretreatment reagent, and (iv) pretreat the organic compounds adsorbed on the strong ion-exchange resin phase in the ion-exchange unit with the trimethylsilylation pretreatment reagent.

(3) The pre-analysis treatment device usable for an amino acid, organic acid, and glucide described above (1) or (2), wherein the ion-exchange unit is configured to supply the dehydration solvent to the solid-phase cartridge through the outlet side of the first nozzle connected to the inlet side of the solid-phase cartridge, before loading the test sample on the solid-phase cartridge.

(4) The pre-analysis treatment device usable for an amino acid, organic acid, and glucide described above in any one of (1) to (3), further includes
at least one cleaning solvent-storing unit for storing a cleaning solvent for cleaning the solid-phase cartridge,
at least one cleaning solvent feed pump for supply of the cleaning solvent from the cleaning solvent-storing unit via the first nozzle to the solid-phase cartridge, and
a switching valve for switching a channel having the first feed pump and a channel having the cleaning solvent feed pump, thereby allowing one of the channels to be communicable with the first nozzle,
wherein the ion-exchange unit is configured to supply the cleaning solvent to the solid-phase cartridge through the outlet side of the first nozzle connected to the inlet side of the solid-phase cartridge, before the test sample is loaded on the solid-phase cartridge.

(5) The pre-analysis treatment device usable for an amino acid, organic acid, and glucide described above in any one of (1) to (4), wherein the derivatization unit is configured to complete withdrawal of the elution solvent, before withdrawing the derivatization reagent by the second feed pump.

(6) The pre-analysis treatment device usable for an amino acid, organic acid, and glucide described above in any one of (1) to (5), wherein the derivatization reagent contains at least one compound selected from N-methyl-N-trimethylsilyltrifluoroacetamide (MSTFA), N,O-bis(trimethylsilyl)trifluoroacetamide (BSTFA), and trimethylchlorosilane (TMCS).

(7) The pre-analysis treatment device usable for an amino acid, organic acid, and glucide described above in (6), wherein the derivatization reagent contains pyridine.

(8) The pre-analysis treatment device usable for an amino acid, organic acid, and glucide described above in any one of (1) to (7), wherein the elution solvent is at least one of hexane and a mixed solution of acetone and hexane.

(9) The pre-analysis treatment device usable for an amino acid, organic acid, and glucide described above in any one of (1) to (8), wherein the strong ion-exchange resin phase comprises at least one resin selected from strong cation-exchange resins, strong anion-exchange resins, and a combination of a strong cation-exchange resin and a strong anion-exchange resin.

(10) The pre-analysis treatment device usable for an amino acid, organic acid, and glucide described above in any one of (1) to (9), wherein the prescribed amount of the derivatization reagent supplied is 0.07 to 2.2 times larger than an apparent volume of the strong ion-exchange resin phase.

(11) A pre-analysis treatment method of pretreating amino acid, organic acid, and glucide, the method includes
loading a test sample on a solid-phase cartridge containing a strong ion-exchange resin phase that adsorbs at least one organic compound selected from amino acids, organic acids, and glucide, thereby allowing the strong ion-exchange resin phase to adsorb the organic compound,
supplying a dehydration solvent to the solid-phase cartridge on which the test sample is loaded, thereby allowing the strong ion-exchange resin phase to be dehydrated,
supplying a prescribed amount of a derivatization reagent to the strong ion-exchange resin phase which the test sample is loaded on and is subsequently dehydrated, and retaining the resulting strong ion-exchange resin phase for a particular time, thereby trimethylsilylating the organic compound adsorbed on the strong ion-exchange resin phase, and simultaneously desorbing the trimethylsilylated organic compound from the strong ion-exchange resin phase, and
supplying a non-ion-exchanging push-out solvent to the solid-phase cartridge where the derivatization reagent is retained, to push the desorbed trimethylsilylated organic compound out of the solid-phase cartridge.

(12) The pre-analysis treatment method for pretreating amino acid, organic acid, and glucide described above in (11), further includes
supplying a prescribed amount of trimethylsilylation pretreatment reagent to the strong ion-exchange resin phase which the test sample is loaded on and is subsequently dehydrated, and retaining the resulting strong ion-exchange resin phase for a particular time, thereby generating a particular isomer of an organic compound adsorbed on the strong ion-exchange resin phase preferentially among multiple isomers possibly generated during trimethylsilylation.

Advantageous Effects of Invention

According to the present invention, it is possible to derivatize at least one organic compound selected from amino acids, organic acids and glucides contained in a test sample, and collect the derivatized compound easily in a short period of tune. It is also possible to automate the pre-analysis treatment of the organic compound easily.

The solution obtained after the pretreatment according to the present invention can be used as it is, in quantitative analysis for example by gas chromatography or liquid chromatography. Therefore, it becomes possible to perform the procedure from collection of test sample to acquisition of quantitative analysis result easily in a short period of time.

BRIEF DESCRIPTION OF THE DRAWINGS

FIG. 1 is a block diagram showing an embodiment of the pre-analysis treatment device according to the present invention in the state where solvents are withdrawn by respective pumps for preparation.

FIG. 2 is a block diagram showing partially the embodiment of the pre-analysis treatment device according to the present invention in the state where the dehydration solvent is supplied via the first nozzle to the solid-phase cartridge for cleaning.

FIG. 3 is a block diagram showing partially the embodiment of the pre-analysis treatment device according to the present invention in the state where the test sample is withdrawn from the sample-storing unit via the first nozzle by the first feed pump.

FIG. 4 is a block diagram showing partially the embodiment of the pre-analysis treatment device according to the present invention in the state where the test sample withdrawn from the first nozzle is supplied to the solid-phase cartridge by the dehydration solvent from the first feed pump and in the state where the dehydration solvent is supplied to the solid-phase cartridge following to the test sample, and the strong ion-exchange resin phase is dehydrated.

FIG. 5 is a block diagram showing partially the embodiment of the pre-analysis treatment device according to the present invention in the state where the derivatization reagent is withdrawn from the derivatization reagent-storing unit via the second nozzle by the second feed pump.

FIG. 6 is a block diagram showing partially the embodiment of the pre-analysis treatment device according to the present invention in the state where the derivatization reagent withdrawn from the second nozzle is supplied to the solid-phase cartridge by the push-out solvent from the second feed pump.

FIG. 7 is a block diagram showing partially the embodiment of the pre-analysis treatment device according to the present invention in the state where the trimethylsilylated organic compounds are pushed out by supply of the push-out solvent to the solid-phase cartridge after retention of the derivatization reagent.

FIG. 8 is a block diagram showing partially another embodiment of the pre-analysis treatment device according to the present invention in the state where the solvents are withdrawn by the respective pumps for preparation.

FIG. 9 is a block diagram showing partially the other embodiment of the pre-analysis treatment device according to the present invention in the state where the pretreatment reagent is withdrawn from the pretreatment reagent-storing unit via the third nozzle by the third feed pump.

FIG. 10 is a block diagram showing partially the other embodiment of the pre-analysis treatment device according to the present invention in the state where the pretreatment reagent withdrawn from the third nozzle is supplied to the solid-phase cartridge with the push-out solvent from the third feed pump.

FIG. 11 shows a GM-CS chromatogram of the trimethylsilylated amino acid-containing solution obtained in Example 1.

FIG. 12 shows a GM-CS chromatogram of the trimethylsilylated glucide-containing solution obtained in Example 2.

FIG. 13 shows a GM-CS chromatogram of the trimethylsilylated glucide-containing solution obtained in Example 3.

FIG. 14 shows a GM-CS chromatogram of the trimethylsilylated glucide-containing solution obtained in Example 3.

DESCRIPTION OF EMBODIMENTS

Hereinafter, favorable embodiments of the pre-analysis treatment device and the pre-analysis treatment, method according to the present invention will be described with reference to drawings. It should be understood that the present invention is not restricted at all by these embodiments below and can be implemented in various forms within the scope of the present invention.

FIG. 1 is an entire block diagram showing an example of the embodiment of the pre-analysis treatment device according to the present invention. The pre-analysis treatment device 1 shown in FIG. 1 comprises, in particular, a sample-storing unit B5 for storing a test sample, a solid-phase cartridge S having a strong ion-exchange resin phase that adsorbs at least one organic compound selected from amino acids, organic acids and glucides that may be contained in a test sample, a dehydration solvent-storing unit B3 for storing a dehydration solvent that dehydrates the strong ion-exchange resin phase on which the test sample is loaded, a first nozzle N1 that is used for discharging the dehydration solvent, or withdrawing or ejecting the test sample, a first feed pump P3 for supplying the dehydration solvent and the test sample via the first nozzle N1 to the solid-phase cartridge S, a derivatization reagent-storing unit B7 for storing a derivatization reagent that trimnethylsilylates the organic compound adsorbed on the strong ion-exchange resin phase, a push-out solvent-storing unit B8 for storing a non-ion-exchanging push-out solvent that pushes the trimethylsilylated organic compound out of the solid-phase cartridge S, a second nozzle N2 that is used for discharging the push-out solvent, or withdrawing or discharging the derivatization reagent, a second feed pump P8 for supplying the derivatization reagent and the push-out solvent via the second nozzle N2 to the solid-phase cartridge S, an ion-exchange unit E configured to withdraw a prescribed amount of the test sample by the first feed pump P3 in a state that the outlet side e1 of the first nozzle N1 is connected to the sample-storing unit B5, then feed the test sample withdrawn, with the dehydration solvent in a state that the outlet side e1 of the first nozzle N1 is connected to an inlet side e3 of the solid-phase cartridge S, load the test sample on the solid-phase cartridge S to allow the strong ion-exchange resin phase to adsorb the organic compound, and then supply the dehydration solvent to dehydrate the strong ion-exchange resin phase, and a derivatization unit D configured to withdraw the prescribed amount of derivatization reagent by the second feed pump P8 in a state that the outlet side e2 of the second nozzle N2 is connected to the derivatization reagent-storing unit B7, feed the prescribed amount of the derivatization reagent with the push-out solvent in a state that the outlet side of the second nozzle is connected to an inlet side e3 of the solid-phase cartridge S, suspend the feed of the elution solvent for a particular time so as to retain the derivatization reagent, thereby trimethylsilylating the organic compound adsorbed on the strong ion-exchange resin phase in the ion-exchange unit E and simultaneously desorbing the trimethylsilylated organic compound from the strong ion-exchange resin phase, and then supply the push-out solvent to push the trimethylsilylated organic compound desorbed out of the solid-phase cartridge S.

As described above in the present invention, a strong ion-exchange resin phase is used as a filler in the solid-phase cartridge. It is thus possible to make at least one organic compound selected from amino acids, organic acids and glucides adsorbed effectively. It is additionally possible to remove water remaining in the strong ion-exchange resin phase easily only by supplying a dehydration solvent, and thus to reduce the adverse influence on subsequent trimethylsilylation significantly.

In addition, the derivatization reagent used in trimethylsilylation of these absorbed organic compounds is designed to be retained in the solid-phase cartridge for a prescribed time. Accordingly, these organic compounds are trimethylsilylated efficiently. Further, these trimethylsilylated organic compounds (hereinafter, referred to as "TMS derivative compounds") desorb from the strong ion-exchange resin phase naturally.

The desorbed TMS derivative compounds are designed to be pushed out with a non-ion-exchanging push-out solvent.

Thus in the present invention, the adsorbed organic compounds are not desorbed and eluted from an ion-exchange resin with the elution medium by ion-exchange interaction, unlike described in Patent Document 1, but the organic compounds adsorbed on the strong ion-exchange resin layer are subjected to derivatization reaction, allowing the derivatized organic compounds to automatically be desorbed. Thus, the derivatized organic compounds can directly be obtained with the push-out solvent. Thus, there is no need for an operation to elute the organic compounds adsorbed on the ion-exchange resin phase once with an ion-exchanging elution solution in such a way as described in Patent Document 1 and it is possible to perform derivatization reliably, as the dehydration treatment can be performed easily and reliably. It is possible in such a configuration to simplify the pre-analysis treatment device and shorten the processing period, while securing the accuracy of the subsequent mass spectrometric analysis and to automate the system easily.

In addition, it is possible to use the solution containing the collected TMS derivative compounds as it is, as the test sample for a gas chromatography mass spectrometer (GC-MS) or a liquid chromatography mass spectrometer (LC-MS), thus enabling construction of an automated system in combination with GC-MS or LC-MS and making the procedure from collection of test sample to acquisition of quantitative analysis results be performed easily in a shorter period of time.

The test sample that is applicable to the present invention is not particularly limited, if the amino acids, organic acids, and glucides contained in the test sample should be quantitatively analyzed comprehensively by the method of metabolome analysis. Examples of such samples include biological body fluids, foods and beverages (including raw meats, vegetables, processed foods and others), culture solutions such as of cells and microbes (excluding foods and beverages), plants (excluding foods and beverages) and the like. Examples of the biological body fluids include blood, lymph, cerebrospinal fluid, saliva, urine, and the like. The test sample is preferably, as needed, prepared as a liquid that can be loaded to the solid-phase cartridge S. For example, a liquid that may contain amino acids, organic acids and glucides is obtained by homogenization or centrifugation treatment.

The amino acid that is applicable to the present invention is not particularly limited, if it has an amino group and a carboxyl group and examples thereof include, but are not limited to, α-amino acids in which an amino group is bound to the carbon to which a carboxyl group is also bonded.

The organic acid that is applicable to the present invention is not particularly limited, if it is an organic compound having a carboxyl group (excluding amino acids and glucides) and examples thereof include carboxylic acids having a carbon number of 1 or more. In particular, those having 2 to 40 carbon atoms are preferable. Examples thereof include formic acid, short-chain fatty acids, medium-chain fatty acids, long-chain fatty acids, aromatic carboxylic acids and the like. The fatty acid may be a saturated or unsaturated fatty acid (either a mono-, bi- or higher-unsaturated fatty acid). It may be a monovalent carboxylic acid or a bivalent or higher carboxylic acid.

The glucide that is applicable to the present invention is not particularly limited, if it is a glucide indicated in the Nutrition Labelling Standards and examples thereof include saccharide (monosaccharides and disaccharides), oligosaccharides of tri- or higher saccharides, polysaccharides, sugar alcohols, citric acid, citrate salts and the like.

A strong ion-exchange resin phase is used as a filler of the solid-phase cartridge for use in the present invention. As described above, efficient adsorption of the amino acids, organic acids and glucides is enabled by the solid-phase cartridge. Such a strong ion-exchange resin phase preferably includes at least one resin selected from the group consisting of strong cation-exchange resins, strong anion-exchange resins and combinations of strong cation- and anion-exchange resins. Examples of the combinations of strong cation- and anion-exchange resins include single solid-phase cartridges containing a mixture of a strong cation-exchange resin and a strong anion-exchange resin or a laminate of the two ion-exchange resins and serial solid-phase cartridges individually containing two different strong ion-exchange resins, and a solid-phase cartridge chosen properly from those above can be used.

The strong cation-exchange resin, as described herein, means a strongly acidic cation-exchange resin and the strong anion-exchange resin means a strongly basic anion-exchange resin.

The resin constituting the strong ion-exchange resin phase is, for example, a resin containing a copolymer of styrene and divinylbenzene as the matrix resin. Such a resin-based ion exchange phase is used, so that amino acids, organic acids and glucides seem to be adsorbed effectively. On the other hand, it was found that the amount of absorption decreases, more significantly when a silica-based ion exchange phase is used than when a resin-based ion-exchange phase is used, depending on the kind of the organic compound.

The strong cation-exchange resin is, for example, a resin in which ion-exchanging groups, i.e., sulfonic acid groups, are bound to the matrix resin described above and the strong anion-exchange resin is, for example, a resin in which ion-exchanging groups, i.e., quaternary ammonium groups, are bound to the matrix resin described above. Use of a strongly acidic or strongly basic ion-exchange resin in this way may be a reason for the effective adsorption of amino acids, organic acids and glucides. On the other hand, it was found that the adsorption amount decreases, more significantly when a weakly acidic or weakly basic ion-exchange resin is used than when a strongly acidic or strongly basic ion-exchange resin is used, depending on the kind of the organic compound.

It is preferable to use, as the filler, a strong cation-exchange resin phase for adsorption of amino acids and a strong anion-exchange resin phase for adsorption of organic acids and glucides.

Examples of the solid-phase cartridges containing such strong cation- and anion-exchange resins as strong ion-exchange resin phase include Smart-SPE CXi-20, Smart-SPE AXi-20 or the like of AiSTI Science Co. Ltd.

The dehydration solvent for use in the present invention is not particularly limited, if it can remove water from the solid-phase cartridge after application of the test sample without any adverse effects on the strong ion-exchange resin phase, amino acids, organic acids, and glucides, but preferably a water-soluble organic solvent from the viewpoint for effective removal of water remaining in the strong ion-exchange resin phase and typical examples thereof include acetonitrile, acetone and the like.

The trimethylsilylation derivatization reagent for use in the present invention is not particularly limited, if it can trimethylsilylate amino acids, organic acids and glucides. Examples of the derivatization reagents include N-methyl-N-trimethylsilyltrifluoroacetamide (MSTFA), N,O-bis(trimethylsilyl)trifluoroacetamide (BSTFA), trimethylchlorosilane (TMCS), N,O-bis(trimethylsilyl)acetamide (BSA), N-methyl-N-trimethylsilylacetamide (MTMSA), N-trimethylsilyldimethylamine (TMSDMA), N-trimethylsilyldiethylamine (TMSDEA), N-trimethylsilylimidazole (TMSI) and the like. These compounds may be used alone or in combination of two or more. In particular from the viewpoint for efficient trimethylsilylation of amino acids, organic acids and glucides, those containing at least one compound selected from MSTFA, BSTFA and TMCS are preferable, and those containing MSTFA and TMCS are more preferable. In this case, the molar ratio of TMCS to MSTFA is preferably 0.5 to 20% from the viewpoint for efficient trimethylsilylation.

The derivatization reagent may contain pyridine from the viewpoint for efficient trimethylsilylation of amino acids, organic acids, and glucides. Pyridine is considered to have a function as a catalyst of trimethylsilylation.

The amount of the derivatization reagent fed to the strong ion-exchange resin phase in the solid-phase cartridge is not particularly limited, but it is preferable, from the viewpoint of easiness in simplifying and automating the operation and also from the viewpoints of influence on the peak shape of GC-MS or LC-MS, stabilized and accurate introduction of the reagent, prevention of damage on mass spectrometer and others, to bring all of the amino acids, organic acids and glucides adsorbed on the strong ion-exchange resin phase into contact with the derivatization reagent only by one supply and minimize the amount of the derivatization reagent passing through the solid-phase cartridge before retention. From the viewpoints above, the amount of the derivatization reagent supplied is preferably 0.07 to 2.2 times larger than the apparent volume of the strong ion-exchange resin phase. The maximum amount supplied is more preferably 1.3 times or less, still more preferably 1.1 times or less from the viewpoint of sharpening the peak shape during GC-MS analysis, although it may vary according to the apparent volume. Alternatively, the minimum amount supplied is more preferably 0.1 time or more from the viewpoint for more stabilized accurate introduction of the reagent. The apparent volume of the strong ion-exchange resin phase, as described herein, is the volume of the solid-phase cartridge in the region where the strong ion-exchange resin phase is filled.

The non-ion-exchanging push-out solvent for use in the present invention is not particularly limited, if it can push the desorbed TMS derivative compounds out of the solid-phase cartridge, but it is preferably hexane or a mixture of acetone and hexane from the viewpoint of stability of the TMS derivative compounds. The mixed solution of acetone and hexane is preferably a mixture of acetone (A) and hexane (H) at a volume-based blending ratio (A/H) of 1/1 to 1/9 for the same reasons.

The first and second feed pumps for use in the present invention are not particularly limited and can be chosen arbitrarily for example according to the amounts of the test sample and others, and examples thereof include tube pumps, syringe pumps, and the like. When the volume of the test sample or the derivatization reagent is very small, it is preferable to use a syringe pump from the viewpoint of accurately control of the discharge rate. In particular, the derivatization unit is configured to withdraw the derivatization reagent via the second nozzle by means of the second feed pump. In this case, if the derivatization reagent remains in the second nozzle or the intermediate channel after being supplied, these may be damaged due to high reactivity of the derivatization reagent. However, if the derivatization unit is configured, for example, to withdraw the push-out solvent into the syringe pump previously, it is possible by using the syringe pump to push out the derivatization reagent with the push-out solvent and thus prevent retention of the derivatization reagent in the nozzle or channel. Such a configuration makes the subsequent cleaning operation easier and thus makes it easier to simplify and automate the pre-analysis treatment device. Such a configuration is particularly effective when multiple test samples are processed continuously.

The pre-analysis treatment device 1 shown in FIG. 1 additionally includes, in addition to the configurations above, as optional configurations, two cleaning solvent-storing units B1 and B2 for storing the cleaning solvents for cleaning the solid-phase cartridge S, two cleaning solvent feed pumps P1 and P2 for supply of the respective cleaning solvents from the cleaning solvent-storing units B1 and B2 via first nozzle N1 to the solid-phase cartridge S, and a switching valve V that connects channel L3 with the first feed pump P3, or channel L1 or L2 each with the cleaning solvent feed pump P1 or P2 to the first nozzle N1 by switching the channel. The ion-exchange unit E is also configured to supply the dehydration solvent with the outlet side e1 of the first nozzle N1 being connected to the inlet side e3 of the solid-phase cartridge S before loading of the test sample on the solid-phase cartridge S and, at the same time, to supply the cleaning solvent with the inlet side e3 of the solid-phase cartridge S being connected to the outlet side e1 of the first nozzle N1 before loading of the test sample on the solid-phase cartridge S. The cleaning, as described above, includes cleaning of the interior of the solid-phase cartridge S and the strong ion-exchange resin phase as the filler, and also adjustment of the state of the strong ion-exchange resin phase (also referred to as conditioning).

The ion-exchange unit E may be configured to supply only at least one cleaning solvent to the solid-phase cartridge S without loading the dehydration solvent on the solid-phase cartridge S before loading the test sample.

As shown in the example of FIG. 1, the ion-exchange unit E has two cleaning solvent-storing units B1 and B2 in addition to the dehydration solvent-storing unit B3, but the number of the cleaning solvent-storing units is not particularly limited and may be one, two or more. The number can be selected properly according to the kinds of the cleaning solvents used for cleaning (conditioning) the interior of the solid-phase cartridge S and the strong ion-exchange resin phase as the filler before loading of the test sample.

The cleaning solvent usable in the present invention is not particularly limited, if it can clean (condition) the strong ion-exchange resin phase and can be chosen properly according, for example, to the kind of the strong ion-exchange resin phase. Examples of the cleaning solvents include ion-exchanged water, acetone, acetonitrile and the like. These solvents may be used alone or in combination of two or more.

In the example shown in FIG. 1, the switching valve V has ports 1 to 4. The port 4, which is connected to the channel L4 that is communicating with the first nozzle N1, is communicable with one of the ports 1 to 3 in the valve L. The ports 1 to 3 are connected respectively to channels L1, L2, and L3. The channels L1 and L2 are respectively provided with cleaning solvent feed pumps P1 and P2, and the channel L3 is provided with first feed pump P3. Communication of the port 4 with the ports 1 to 3 can be switched, for example, with a solenoid valve.

The cleaning solvent feed pumps P1 and P2, the cleaning solvent-storing units B1 and B2 and the switching valve V, and also the first feed pump P3, the dehydration solvent-storing unit B3 and the switching valve V, are communicable via valves v1 that can supply the respective liquids in the direction indicated by the arrows in FIG. 1. The second feed pump P8 and the push-out solvent-storing unit B8 are communicable via a valve v2 that can supply the liquid in the direction indicated by the arrow shown in FIG. 1.

Operation of the pumps P1 to P3 and P8, the switching valve V and the valves v1 and v2 is controllable by the solvent control unit.

In the example shown in FIG. 1, the pre-analysis treatment device further includes a cartridge-holding means A for holding and fixing the solid-phase cartridge S at a predetermined position. The cartridge-holding means A may be configured to have an additional solid-phase cartridge S for continuous pretreatment.

The pre-analysis treatment device further includes a container-storing means C for storing a waste liquid-storing unit B4 for collection of the dehydration solvent, cleaning solvent, and test sample discharged from the solid-phase cartridge S, a sample-storing unit B5 for storing the test sample, an analysis solution-storing unit B6 for collection of the TMS derivative compound-containing solution and a derivatization reagent-storing unit B7 for storing the derivatization reagent.

In the pre-analysis treatment device according to the present invention, the solid-phase cartridge S becomes communicative with the waste liquid-storing unit B4 during ion exchange in the ion-exchange unit E and then, the solid-phase cartridge S becomes communicative with the analysis solution-storing unit B6 during trimethylsilylation in the derivatization unit D. Thus, from the viewpoint of easiness in automation, the solid-phase cartridge S or the waste liquid-storing unit B4 and the analysis solution-storing unit B6 are preferably moved. In such a case, the solid-phase cartridge S may be moved or the waste liquid-storing unit B4 and the analysis solution-storing unit B6 may be moved. In the present embodiment, a case where the solid-phase cartridge S is moved will be described below as an example. In this case, the cartridge-holding means A has a holding unit (not shown in the Figure) holding and fixing the solid-phase cartridge S at positions respectively corresponding to the waste liquid-storing unit B4 and the sample-storing unit B5. The holding unit is configured to move according to the operation of the solid-phase cartridge S. It is preferable that the movement of the solid-phase cartridge S is performed by a moving means and the moving means is controlled by a movement control unit.

In the ion-exchange unit of the pre-analysis treatment device according to the present invention, the first nozzle is connected to the solid-phase cartridge, and is used for withdrawal of a test sample from the sample-storing unit, while the second nozzle is connected to the solid-phase cartridge, and is used for withdrawal of a derivatization reagent from the derivatization reagent-storing unit. Thus, the first and second feed nozzles are preferably connected respectively to the sample-storing unit and derivatization reagent-storing unit in addition to the solid-phase cartridge. In this case, preferably each nozzle is moved from the viewpoint of easiness of simplification and automation of the instrument and more preferably each nozzle is configured to be moved by the same moving means and the operation is controlled by a movement control unit. If the solid-phase cartridge is moved as described above, preferably it is moved by a common moving means and movement of the moving means controlled by a common movement control unit.

The solvent control unit and the movement control unit described above are preferably configured to be controlled by a central control unit. The central control unit includes, for example, a central processing unit of executing particular processing, a Random Access Memory (RAM) storing data temporarily, memory units such as Read Only Memory (ROM), and a hard disk that store particular control programs and peripheral circuits of these devices (none of them is shown in Figure). The central control unit executes the control programs stored in the memory unit and thus functions as the solvent control unit and the movement control unit. The solvent control unit and the movement control unit are configured to control operations of the ion-exchange unit and the derivatization unit.

Hereinafter, examples of the operation of the pre-analysis treatment device 1 shown in FIG. 1 will be described with reference to FIGS. 1 to 7. The pre-analysis treatment device 1 shown in FIG. 1 is configured to perform a preparation step, a cleaning step, an adsorption step, a dehydration step, a derivatization step, and a push-out step before termination of the pre-analysis treatment of the test sample. It is also configured that the preparation step is performed by activation of the ion-exchange unit E and the derivatization unit D, the cleaning, adsorption, and dehydration steps are performed by activation of the ion-exchange unit E, and the derivatize and push-out steps are performed by activation of the derivatization unit D.

FIG. 1 shows the state where the pre-analysis treatment device 1 performs the preparation step. Then in the ion-exchange unit E, each of the pumps P1 to P3 is activated for withdrawal of each solvent in the state that each port of the switching valve V is closed and each valve v1 is adjusted so that the pumps P1 to P3 become communicable respectively with cleaning solvent-storing units B1 and B2 and dehydration solvent-storing unit B3. Alternatively, in the derivatization unit D, the pump P8 is activated for withdrawal of the push-out solvent in the state that the valve v2 is so adjusted that the pump P8 becomes communicable with the push-out solvent-storing unit B8. The solid-phase cartridge S is moved by a moving means (not shown in drawings, the same shall apply hereinafter) to the position where the solvent and others passing through it can be discharged to the waste liquid-storing unit B4 and held and fixed by the holding unit of the cartridge-holding means A. When the solid-phase cartridge S is placed at a prescribed position and each pump withdraws the liquid in a prescribed amount, the preparation step is completed.

A cleaning step is performed after completion of the preparation step. In the cleaning step, each cleaning solvent is fed one by one via the first nozzle 1 into the solid-phase cartridge S. FIG. 2 shows a state where the solid-phase cartridge is cleaned with the dehydration solvent after it is cleaned with two kinds of cleaning solvents. Specifically, the cleaning step is performed in the following order. First, the first nozzle N1 is moved by the moving means so that the outlet side e1 thereof is connected to the inlet side e3 of the solid-phase cartridge S. The switching valve V is switched so that port 4 and port 1 become communicable. The pump P1 that withdraws the first cleaning solvent is then activated to feed the solvent in a prescribed amount, cleaning the strong ion-exchange resin phase in the solid-phase cartridge S with the first cleaning solvent. After supply of the prescribed amount of cleaning solvent, the pump P1 is stopped and the switching valve V is switched so that the ports 4 and 2 become communicable. The pump P2 that withdraws the second cleaning solvent is then activated to feed the solvent in a prescribed amount, cleaning the strong ion-exchange resin phase in the solid-phase cartridge S with the second cleaning solvent. After supply of the prescribed amount of cleaning solvent, the pump P2 is stopped and the switching valve V is switched so that ports 4 and 3 become communicable. The pump P3 that withdraws the dehydration solvent is then activated to feed the solvent in a prescribed amount, cleaning the strong ion-exchange resin phase in the solid-phase cartridge S with the dehydration solvent. After supply of the prescribed amount of the solvent, the pump P3 is stopped. Each solvent that has passed then is discharged into the waste liquid-storing unit B4. Thus, the cleaning step is completed. An example of the combination of the solvents is water (first cleaning solvent), acetone (second cleaning solvent), and acetonitrile (dehydration solvent), but the combination is not limited thereto.

An adsorption step is performed after completion of the cleaning step. In the adsorption step, a test sample is withdrawn and loaded onto the strong ion-exchange resin phase in the solid-phase cartridge S. At least one organic compound selected from amino acids, organic acids, and glucides that may be contained in the test sample is adsorbed. More specifically, the adsorption step proceeds in the following manner: After completion of the cleaning step, the first nozzle N1 is moved by the moving means (not shown in the drawings) so that the outlet side e1 thereof is connected to the sample-storing unit B5. The pump P3 is then activated and a prescribed amount of test sample is withdrawn by the pump P3. FIG. 3 shows this state. After withdrawal of the prescribed amount of test sample, the pump P3 is stopped. The first nozzle N1 is then moved again by the moving means (not shown in the drawings) so that the outlet side e1 thereof is connected to the inlet side e3 of the solid-phase cartridge S and the pump P3 is reactivated, discharging the prescribed amount of the adsorbed test sample with the dehydration solvent. FIG. 4 shows this state. Thus, the adsorption step is completed. As needed, the pump P3 may be stopped.

A dehydration step is performed after completion of the adsorption step. In the dehydration step, a dehydration solvent is supplied to the solid-phase cartridge S on which the test sample is loaded, dehydrating the strong ion-exchange resin phase. FIG. 4 shows this state. If the pump P3 is stopped in the adsorption step, the pump P3 is activated. If it is not stopped, the dehydration solvent is supplied continuously from the adsorption step. After supply of the dehydration solvent in a prescribed amount, the pump P3 is stopped. The first nozzle N1 is then moved by the moving means away from the inlet side e3 of the solid-phase cartridge S. Thus, the dehydration step is completed.

Thus, in the present invention, it is possible to remove easily water contained in the test sample from the strong ion-exchange resin phase to a degree that the derivatization is substantially unaffected, only by supplying the dehydration solvent to the strong ion-exchange resin in the state where at least one organic compound selected from amino acids, organic acids and glucides is adsorbed thereon. It is accordingly possible to derivatize these organic compounds reliably in the derivatization step.

A derivatization step is performed after completion of the dehydration step. In the derivatization step, a prescribed amount of the derivatization reagent is supplied to the strong ion-exchange resin phase and left there for a particular time. More specifically the derivatization step proceeds in the following manner. After completion of the dehydration step, the solid-phase cartridge S is moved by the moving means to a position where the solution that has passed through the solid-phase cartridge S can be discharged into the analysis solution-storing unit B6 and held and fixed by another holding unit of the cartridge-holding means A (not shown in drawings). The second nozzle N2 is then moved by the moving means so that the outlet side e2 thereof is connected to the derivatization reagent-storing unit B7. The second feed pump P8 is then activated, and the derivatization reagent is withdrawn. FIG. 5 shows this state. The pump P8 is stopped after withdrawal of the derivatization reagent in a prescribed amount. The second nozzle N2 is moved again by the moving means so that the outlet side e2 thereof is connected to the inlet side e3 of the solid-phase cartridge S. The second feed pump P8 is then activated, and the prescribed amount of the adsorbed derivatization reagent is pushed out with the non-ion-exchanging push-out solvent and supplied to the strong ion-exchange resin phase. FIG. 6 shows this state. After supply of a prescribed amount of the derivatization reagent, the pump P8 is stopped. It is possible in this way to make the derivatization reagent remain in the strong ion-exchange resin phase. It is possible, by making the derivatization reagent remain there for a particular time, to trimethylsilylate at least one organic compound selected from amino acids, organic acids, and glucides adsorbed on the strong ion-exchange resin and desorb it from the strong ion-exchange resin. Thus, there is no need for using a common ion-exchanging elution solvent, which makes it easier to simplify the instrument, shorten the treatment period, and automate the procedure. After retention of the derivatization reagent for a particular time, the derivatization step is completed.

A push-out step is performed after completion of the derivatization step. In the push-out step, a non-ion-exchanging push-out solvent is supplied to the solid-phase cartridge S that contains the retained derivatization reagent, pushing out the desorbed TMS derivative compound from the solid-phase cartridge S. More specifically the push-out step proceeds in the following manner: After completion of the derivatization step, the push-out solvent is supplied in a prescribed amount by activating the pump P8, which had withdrawn the push-out solvent in the preparation step. The desorbed TMS derivative compound is thus pushed out with the push-out solvent from the solid-phase cartridge S and discharged into the analysis solution-storing unit B6. FIG. 7 shows this state. After supply of the prescribed amount of the push-out solvent, the pump P8 is stopped. Thus, the push-out step is completed.

In the case of the present embodiment, it is possible, by withdrawing the push-out solvent previously into the pump P8 and pushing out the withdrawn derivatization reagent with the push-out solvent, to prevent retention of the derivatization reagent in the channel L8. Accordingly, it becomes easier to prevent damaging of the channel L8 and the valve v2 by the highly reactive derivative reagent. It is also possible to simplify channel cleaning, thus making it easier to simplify and automate the instrument. It also makes it easier to conduct analytical pretreatment of multiple samples.

A volume-adjusting step may be performed, as needed, after completion of the push-out step. The volume-adjusting step is a step of adjusting the TMS derivative compound-containing analysis solution discharged into the analysis solution-storing unit B6 to a desired volume. More specifically the volume-adjusting step proceeds in the following manner: The nozzle N2 is separated from the solid-phase cartridge S by the moving means. The solid-phase cartridge S is then moved by the moving means from the position where the solution passing through the solid-phase cartridge S can be discharged into the analysis solution-storing unit B6. The solid-phase cartridge S may be transferred to a disposal site which accepts a used cartridge (not shown in drawings). The push-out solvent is supplied to be a desired volume, for example, as the nozzle N2 is connected to the analysis solution-storing unit B6 by the moving means and the pump P8 is activated by the derivatization unit D. When the desired volume is reached, the pump P8 is stopped. Thus, the volume-adjusting step is completed. It may be configured, in the ion-exchange unit E, that the pumps P1 to P3 are activated according to the kinds of the solvents used for volume adjustment, so as to supply the solvents previously withdrawn.

Hereinafter, other embodiments of the pre-analysis treatment device and the pre-analysis treatment method according to the present invention will be described with reference to drawings.

FIG. 8 is a block diagram showing partially the pre-analysis treatment device 2 in the present embodiment. The pre-analysis treatment device 2 has a configuration substantially identical with that of the pre-analysis treatment device 1 shown in FIG. 1, except that it has a trimethylsilylation pretreatment unit F, and that the container-storing means C has additionally a pretreatment reagent-storing unit B10 storing the trimethylsilylation pretreatment reagent. Accordingly, the same reference signs are allocated to the same constitutional units and only constitutional units different from those in the pre-analysis treatment device 1 will be described below.

The "trimethylsilylation pretreatment reagent," as used in the present invention, means a reagent used for pretreatment of the organic compounds described above before trimethylsilylation of the organic compounds in the derivatization unit.

The pre-analysis treatment device 2 of the present embodiment includes, in addition to the constitutional units in the pre-analysis treatment device 1 shown in FIG. 1, a pretreatment reagent-storing unit B10, a third nozzle N4, a third feed pump P9, and a trimethylsilylation pretreatment unit F. The pretreatment reagent-storing unit B10 stores a trimethylsilylation pretreatment reagent for preferential generation of a particular isomer of an organic compound among multiple isomers generated during trimethylsilylation (hereinafter, referred to as "TMS-derivatization pretreatment reagent"). The third nozzle N4 withdraws or ejects the TMS-derivatization pretreatment reagent. The third feed pump P9 supplies the TMS-derivatization pretreatment reagent via a third nozzle N4 to the solid-phase cartridge S. The trimethylsilylation pretreatment unit F is configured to withdraw a prescribed amount of the pretreatment reagent by the third feed pump P9 in a state that the outlet side e4 of the third nozzle N4 is connected to the pretreatment reagent-storing unit B10, deliver the prescribed amount of TMS-derivatization pretreatment reagent in a state that it is connected to the inlet side e3 of the solid-phase cartridge S, make the TMS-derivatization pretreatment reagent remain there by terminating the liquid supply for a particular time, and thus pretreat the organic compounds adsorbed on the strong ion-exchange resin phase in the ion-exchange unit E, with the TMS-derivatization pretreatment reagent. Thus, the trimethylsilylation pretreatment unit in the present invention is configured to perform pretreatment of the organic compounds adsorbed on the strong ion-exchange resin phase in the solid-phase cartridge with a prescribed reagent before the trimethylsilylation in the derivatization unit D.

It is possible in such a configuration to trimethylsilylate the TMS-derivatization-pretreated organic compounds adsorbed on the strong ion-exchange resin phase after the organic compounds adsorbed on the strong ion-exchange resin phase in the solid-phase cartridge are trimethylsilylation-pretreated (hereinafter, referred to as "TMS-derivatization pretreated" in some cases). It is thus possible to conduct the TMS-derivatization pretreatment and derivatization efficiently. It is also possible to obtain particular isomers of trimethylsilylated organic compounds preferentially and efficiently.

For example, if the organic compounds have isomers in the chemical equilibrium relationship or produce multiple isomers during trimethylsilylation, the trimethylsilylated isomers may exhibit different peaks and have the same retention times with other organic compounds during chromatographic measurement conducted after pre-analysis treatment, depending on the kind of the derivatization reagent and the kinds of the organic compounds, and the chemical equilibrium may be disturbed after collection of the test sample. Thus, depending on the kind of the derivatization reagent or the kind of the organic compounds, it may be possible to determine the compounds described above more accurately, when analysis is made after isomers present in the chemical equilibrium relationship are converted into particular isomers before trimethylsilylation or particular isomers are formed preferentially by conducting a pretreatment for prevention of generation of multiple isomer during trimethylsilylation. The present embodiment is favorable in such a situation.

The active component in the TMS-derivatization pretreatment reagent usable in the present invention is not particularly limited, if it can give particular isomers of trimethylsilylated organic compounds preferentially among the multiple isomers of the organic compounds during trimethylsilylation, and can be chosen properly, for example, according to the kinds of the organic compounds and the derivatization reagent. It becomes possible by performing the TMS-derivatization pretreatment with the TMS-derivatization pretreatment reagent, for example, to obtain particular isomers of trimethylsilylated organic compounds preferentially among isomers of the organic compounds in the chemical equilibrium relationship and to obtain particular isomers of trimethylsilylated organ compounds preferentially by preventing generation of multiple isomers thereof during trimethylsilylation. For example, fructose is considered to be in chemical equilibrium among cyclic-structured β-fructopyranose, β-fructofuranose and α-fructofuranose and a small amount of other structures including chain structures and it is possible, by conducting the TMS-derivatization pretreatment, to convert the cyclic-structured isomers to linear chain structures by ring opening, so as to obtain chain-structured trimethylsilylated organic compounds preferentially. For another example, the inventors have found that, although sucrose gives multiple isomers, when being trimethylsilylated, it is possible by conducting the TMS-derivatization pretreatment to obtain particular isomers of trimethylsilylated organic compounds preferentially.

Such a reagent more preferably contains, as the active component, a nitrogen-containing compound, more preferably an amine compound. Favorable examples of the amine compounds include alkoxyamines and the salts thereof (including hydrochloride salts). Examples of the alkoxyamines and the salts thereof (including hydrochloride salts) include methoxyamine and the salts thereof (including hydrochloride salt) (hereinafter, referred to as "methoxyamine or the like") and the like. In the present invention, the TMS-derivatization pretreatment performed by using a reagent containing methoxyamine or the like will be referred to as methoxim derivatization treatment, and the TMS-derivatization pretreatment reagent as methoxim derivatization reagent.

The concentration of the nitrogen-containing compound in the pretreatment reagent is not particularly limited, but preferably 5 to 10% from the viewpoint of preferential production of particular isomers.

The TMS-derivatization pretreatment reagent preferably contains a solvent that can dissolve the nitrogen-containing compound. Examples of the solvents include pyridine, acetonitrile, acetone, chloroform, dichloromethane, and the like. In particular, a solvent of a nitrogen-containing organic compound, such as pyridine or acetonitrile, is preferably used. These solvents may be used alone or as a mixture of two or more.

Hereinafter, a case where an amine compound, in particular methoxyamine or the like, is used as the active component of the TMS-derivatization pretreatment reagent will be described. A study by the inventor has shown that methoxyamine or the like is less soluble in the solvent pyridine, and only a pyridine solution containing 2% methoxyamine or the like can be obtained. At such a low concentration, it was possible to some extent to obtain particular isomers preferentially among multiple isomers possibly generated during trimethylsilylation, but there was still room for improvement. Because pyridine functions as a catalyst during derivatization of the organic compound as described above, it is favorable as the solvent for the TMS-derivatization pretreatment reagent.

However, a study by the inventors has shown that it was possible to obtain a 10% solution of methoxyamine or the like by using a mixed solvent of pyridine and acetonitrile. It was also found that, when the blending ratio was properly adjusted, it was possible to obtain derivatives of particular isomers only by using a TMS-derivatization pretreatment reagent (methoxim derivatization reagent) in a small amount. In this case, the blending ratio of pyridine (P) to acetonitrile (A) (P/A, volume standard) was preferably 3/1 to 10/1, more preferably 4/1 to 9/1, particularly preferably 8/1 to 9/1.

The amount of the TMS-derivatization pretreatment reagent fed into the strong ion-exchange resin phase of the solid-phase cartridge is not particularly limited, but it is preferable that all of the amino acids, organic acids and glucides adsorbed on the strong ion-exchange resin phase become in contact with the TMS-derivatization pretreatment reagent only by a single supply thereof, and the amount of the TMS-derivatization pretreatment reagent that passes through the solid-phase cartridge before retention is preferably minimized. Accordingly, the amount of the TMS-derivatization pretreatment reagent supplied is preferably 0.07 to 2.2 times larger than the apparent volume of the strong ion-exchange resin phase. The maximum amount is more preferably 1.3 times or less, still more preferably 1.1 times or less, from the viewpoint of the sharpness of the peak shape in GC-MS analysis, although it may vary according to the apparent volume. Alternative, the minimum amount is more preferably 0.1 time or more from the viewpoint of more stabilized accurate introduction of the reagent.

The third feed pump for use in the present invention may have a configuration similar to that of the second feed pump described above. When the TMS-derivatization pretreatment reagent is highly reactive as the derivatization reagent, use of a syringe pump is preferable, as described above.

The pre-analysis treatment device 2 shown in FIG. 8 includes, as an optional constitutional unit, a push-out solvent-storing unit B9 for discharge of the pretreatment reagent withdrawn from the pretreatment reagent-storing unit B10. The push-out solvent used may be identical with that used in the pre-analysis treatment device 1. The third feed pump P9 and the push-out solvent-storing unit B9 are configured to be communicable with each other via a valve v3 that can supply the liquid in the direction indicated by the arrow shown in FIG. 8. Operation of the pump P9 and the valve v3 is controllable by the solvent control unit similarly to the operation of the pre-analysis treatment device 1. The third nozzle N4 is connected to the solid-phase cartridge S and withdraws the push-out solution from the pretreatment reagent-storing unit B10. Thus, the third nozzle N4 is preferably connected to the solid-phase cartridge S and also to the pretreatment reagent-storing unit B10. In this case, it is preferable from the viewpoint of easiness of simplifying and automating the device that the third nozzle N4 is moved by a moving means that is also used for the first and second nozzles, like in the pre-analysis treatment device 1. It is more preferable that the operation is controlled by the movement control unit.

Hereinafter, examples of the operation of the pre-analysis treatment device 2 shown in FIG. 8 will be described with reference to FIGS. 9 and 10.

The pre-analysis treatment device 2 shown in FIG. 8 is configured to perform a preparation step, a cleaning step, an adsorption step, a dehydration step, a TMS-derivatization pretreatment step, a derivatization step and a push-out step before pre-analysis treatment of the test sample is completed. It is also configured that the preparation step is performed by activation of the ion-exchange unit E, the TMS-derivatization pretreatment unit F and the derivatization unit D; the cleaning step, the adsorption step, and the dehydration step by activation of the ion-exchange unit E; the TMS-derivatization pretreatment step by activation of the TMS-derivatization pretreatment unit F; and the derivatization step and the push-out step by activation of the derivatization unit D. Hereinafter, operation of the TMS-derivatization pretreatment unit F, which is configured differently from the pre-analysis treatment device 1 shown in FIG. 1, will be described.

FIG. 8 shows a state where the pre-analysis treatment device 2 is performing the preparation step. In the TMS-derivatization pretreatment unit F, the valve v3 is adjusted in such a manner that the pump P9 and the push-out solvent-storing unit B9 are in the communicating state, and then the pump P9 is activated to withdraw the push-out solvent. Other operations are performed similarly to the pre-analysis treatment device 1 and the preparation step is completed. After completion of the preparation step, the cleaning step, the adsorption step and the dehydration step are performed sequentially, as described above.

A TMS derivatization pretreatment step is performed after completion of the dehydration step. In the TMS derivatization pretreatment step, a prescribed amount of the TMS-derivatization pretreatment reagent is supplied to the strong ion-exchange resin phase and left there for a particular time. More specifically, the TMS derivatization pretreatment step proceeds in the following manner: After completion of the dehydration step, the solid-phase cartridge S is moved by the moving means to a position where the solution that passes through the solid-phase cartridge S can be discharged to the analysis solution-storing unit B6, and is held and fixed by another holding unit (not shown in drawings) of the cartridge-holding means A. The third nozzle N4 is moved by the moving means and the outlet side e4 thereof is connected to the pretreatment reagent-storing unit B10. The third feed pump P9 is then activated and the TMS-derivatization pretreatment reagent is withdrawn. FIG. 9 shows this state. The pump P9 is stopped after a prescribed amount of the liquid is withdrawn. The third nozzle N4 is moved again by the moving means, and the outlet side e4 thereof is connected to the inlet side e3 of the solid-phase cartridge S. The third feed pump P9 is then activated to push out the prescribed amount of the TMS-derivatization pretreatment reagent withdrawn, with the non-ion-exchanging push-out solvent, so as to supply the TMS-derivatization pretreatment reagent to the strong ion-exchange resin phase. FIG. 10 shows this state. After supply of a prescribed amount of the TMS-derivatization pretreatment reagent, the pump P9 is stopped. It is possible in this way to make the TMS-derivatization pretreatment reagent remain in the strong ion-exchange resin phase. The TPS-derivatization pretreatment reagent is left there for a particular time, thereby pretreating at least one organic compound selected from amino acids, organic acids and glucides adsorbed on the strong ion-exchange resin. It is possible in this way to generate preferentially a particular isomer (a trimethylsilylated organic compound) of an organic compound among multiple isomers which may be generated during trimethylsilylation.

In the case of the present embodiment, it is possible to prevent retention of the TMS-derivatization pretreatment reagent in the channel L9, by withdrawing the push-out solvent previously to the pump P9 and then pushing out the withdrawn TMS-derivatization pretreatment reagent with the elution solvent. Thus, it becomes easier to prevent the channel L9 and the valve v3 to be damaged by the highly reactive derivative reagent. It also becomes easier to clean the channel and thus further easier to simplify and automate the device. It also becomes easier to perform pre-analysis treatment of multiple samples.

A derivatization step is performed after completion of the TMS derivatization pretreatment step. As the solid-phase cartridge S is moved previously to a predetermined position and held and fixed there in this embodiment, unlike the case of the pre-analysis treatment device 1, the second nozzle N2 is moved by the moving means after termination of the TMS-derivatization pretreatment step, and the outlet side e2 thereof is connected to the derivatization reagent-storing unit B7. The derivatization step and the push-out step are then performed, like the case of the pre-analysis treatment device 1. A volume-adjusting step or the like may be performed depending on the necessity as described above.

EXAMPLES

Example 1

An amino acid solution containing (1) alanine, (2) valine, (3) leucine, (4) isoleucine, (5) proline, (6) glycine, (7) serine, (8) threonine, (9) aspartic acid, (10) methionine, (11) oxoproline, (12) glutamic acid, (13) phenylalanine, (14) lysine, (15) tyrosine, and (16) cystine was prepared as the test sample.

A mixed reagent containing a mixed solution of MSTFA and TMCS (MSTFA:TMCS=99:1) and pyridine (mixed solution:pyridine=5:1, volume ratio) was prepared as the trimethylsilylation derivatization reagent.

A solid-phase cartridge containing a strong cation-exchange resin phase (Smart-SPE CXi-20 produced by AiSTI Science Co. Ltd, apparent volume: 45 mm$^3$) was made available. 1 mL of ion-exchange water was supplied to the solid-phase cartridge as the first cleaning solvent; 1 mL of acetone was then supplied thereto as the second cleaning solvent; 1 mL of acetonitrile was then supplied thereto as the dehydration solvent, thus cleaning the strong cation-exchange resin phase in the solid-phase cartridge (cleaning step).

Then, 0.2 mL of the amino acid solution was loaded on the solid-phase cartridge, making the amino acids be adsorbed on the strong cation-exchange resin phase (adsorption step). Subsequently, 0.5 mL of the dehydration solvent was supplied thereto, dehydrating the strong cation-exchange resin phase (dehydration step).

Then, 60 μL of the mixed reagent was loaded to the solid-phase cartridge and allowed to remain there for 1 minute (derivatization step). Then, 0.94 mL of a mixed solution of acetone (A) and hexane (H) (A/H=15/85) was supplied thereto as the push-out solvent, pushing the desorbed trimethylsilylated amino acids out of the solid-phase cartridge and collecting the solution in a test tube (push-out step). The push-out solvent was supplied thereto for adjustment of volume, to obtain 1 mL of a test sample solution.

It took approximately 5 minutes to obtain the test sample solution from the cleaning step.

25 μL of the test sample solution was injected into a gas chromatography mass spectrometer (Agilent 7890/5975C manufactured by Agilent Technologies) for mass spectrometric analysis. The analysis condition at this time will be described below. Analytical result is shown in FIG. 11. In FIG. 11, peaks of numbers 1 to 16 correspond to the trimethylsilylated compounds of amino acids (1) to (16).

<GC-MS Analysis Condition>
PTV Injector: LVI-S200 (AiSTI Science Co. Ltd.); Stomach Insert
Injector Temp.: 70° C. (0.3 min)-120° C./min-290° C. (18 min)
Auto Sampler: Agilent 7683 (Agilent Co. Ltd.); 50 μL Syringe
Injector Volume: 25 μL
Injector Speed: Slow
Column: DB-5 MS, 0.25 mm i.d.×30 m, df; 0.25 μm
Column Oven Temp.: 60° C. (4 min)-15° C./min-300° C. (3 min)
Inlet Mode: Solvent Vent Mode
Vent Flow: 150 mL/min
Vent Press: 70 kPa
Vent End Time: 0.27 min
Purge Flow: 50 mL/min
Purge Time: 4 min
Gas Saver Flow: 20 mL/min
Gas Saver Time: 6 min
Detector Temp.: 290° C.
MS Method: SCAN; 50-450 m/z Example 2

A solution containing ribitol, fructose, citrate, and sucrose was prepared as the test sample and the solution was diluted 50 times with acetonitrile. The resulting solution was used as the glucide solution.

The derivatization reagent used was the same as that used in Example 1.

A solid-phase cartridge containing a strong anion-exchange resin phase (Smart-SPE AXi-20 produced by AiSTI Science Co. Ltd, apparent volume: 45 mm$^3$) was made available; 2 mL of ion-exchanged water was supplied to the solid-phase cartridge as the first cleaning solvent; 2 mL of acetone was then supplied thereto as the second cleaning solvent; and 2 mL of acetonitrile was then supplied thereto as the dehydration solvent, cleaning the strong anion-exchange resin phase in the solid-phase cartridge (cleaning step).

Then, 1 mL of the glucide solution was loaded to the solid-phase cartridge, making the glucides be adsorbed on the strong anion-exchange resin phase (adsorption step). Subsequently 1 mL of the dehydration solvent was supplied thereto, dehydrating the strong anion-exchange resin phase (dehydration step).

Then, 60 μL of the mixed reagent was loaded to the solid-phase cartridge and allowed to remain there for 1 minute (derivatization step). Then, 0.94 mL of a mixed solution of acetone (A) and hexane (H) (A/H=15/85) was supplied thereto as the push-out solvent, pushing out the desorbed trimethylsilylated glucides from the solid-phase cartridge and collecting the solution in a test tube (push-out step). The push-out solvent was supplied thereto for adjustment of volume, to obtain 1 mL of a test sample solution.

It took approximately 5 minutes to obtain the test sample solution from the cleaning step.

25 μL of the test sample solution was subjected to mass spectrometric analysis in a manner similar to Example 1. Analytical result is shown in FIG. 12.

Comparative Example 1

Pre-analysis treatment was performed in a manner similar to Example 2, except that a solid-phase cartridge containing a weak anion-exchange resin phase (Smart-SPE WAXi-20 manufactured by AiSTI Science Co. Ltd, apparent volume: 45 mm$^3$) was used as the solid-phase cartridge, to obtain 1 mL of a test sample solution. 25 μL of the test sample solution was subjected to mass spectrometric analysis in a manner similar to Example 1. Analytical result is shown in Table 1, wherein the numbers are relative values compared to the peak values of the TMS-derivatized glucides in Example 2.

Comparative Example 2

Pre-analysis treatment was performed in a manner similar to Example 2, except that a solid-phase cartridge containing a silica-based filler phase (Smart-SPE SAX-30 manufactured by AiSTI Science Co. Ltd, apparent volume: 68 mm$^3$) was used as the solid-phase cartridge, to obtain 1 mL of a test sample solution. 25 μL of the test sample solution was subjected to mass spectrometric analysis in a manner similar to Example 1. Analytical result is shown in Table 1, wherein the numbers are relative values compared to the peak values of the TMS-derivatized glucides in Example 2.

TABLE 1

| Peak number | TMS—derivatized sugar | Example 2 | Comparative Example 1 | Comparative Example 2 |
|---|---|---|---|---|
| 1 | Ribitol—5TMS | 100 | 10 | 66 |
| 2 | Fructose—5TMS | 100 | 13 | 86 |
| 3 | Citrate—3TMS | 100 | 112 | 59 |
| 4 | Sucrose—8TMS | 100 | 118 | 77 |

FIGS. 11 and 12 show that, when a solution containing various amino acids and glucides is used as the test sample, it is possible, by using the pre-analysis treatment method according to the present invention, to collect trimethylsilylated amino acids and glucides that are contained in the test sample solution.

Table 1 also shows that various trimethylsilylated glucides can be detected at higher sensitivity in Example 2 (strong ion-exchange resin phase) than in Comparative Examples 1 and 2.

The results above show that the pre-analysis treatment method according to the present invention is favorably suited to metabolome analysis that demands comprehensive and quantitative analysis. Accordingly, the pre-analysis treatment device according to the present invention, which can employ this processing method, is expected to permit execution of the pre-analysis treatment for metabolome analysis easily in a short period of time and easy automation of the device.

Example 3

A solution containing fructose and sucrose (0.2 mM in total) was prepared as the test sample and the solution was diluted 50 times with acetonitrile. The resulting solution was used as the glucide solution.

The TMS-derivatization pretreatment reagent (methoxim derivatization reagent) used was 10 vol % methoxyamine solution. The solvent of the solution was a mixed solution of pyridine (P) and acetonitrile (A) (P/A=9/1).

The derivatization reagent used was MSTFA (concentrate solution).

A solid-phase cartridge containing a strong cation-exchange resin phase (Smart-SPE AXi-20 manufactured by AiSTI Science Co. Ltd) was made available; 2 mL of ion-exchanged water was supplied to the solid-phase cartridge as the first cleaning solvent; 2 mL of acetone was then supplied thereto as the second cleaning solvent; 2 mL of acetonitrile was then supplied thereto as the dehydration solvent, cleaning the strong cation-exchange resin phase in the solid-phase cartridge (cleaning step).

Then, 1 mL of the glucide solution was loaded to the solid-phase cartridge, making the glucides be adsorbed on the strong anion-exchange resin phase (adsorption step). Subsequently, 1 mL of the dehydration solvent was supplied thereto, dehydrating the strong anion-exchange resin phase (dehydration step).

Then, 30 μL of the pretreatment reagent was loaded to the solid-phase cartridge and allowed to remain there for 2 minutes (TMS-derivatization pretreatment (methoxim derivatization treatment) step).

Then, 50 μL of the derivatization reagent was loaded to the solid-phase cartridge and allowed to remain there for 1 minute (derivatization step). Then, 0.92 mL of a mixed solution of acetone (A) and hexane (H) (A/H=15/85) was supplied thereto as the push-out solvent, pushing out the desorbed trimethylsilylated glucides out of the solid-phase cartridge and collecting the solution in a test tube (push-out step). The push-out solvent was then supplied thereto for adjustment of volume, to obtain 1 mL of a test sample solution.

It took approximately 5 minutes to obtain the test sample solution from the cleaning step.

25 μL of the test sample solution was subjected to mass spectrometric analysis in a manner similar to Example 1. Analytical result is shown in FIG. 13.

Comparative Example 3

Pre-analysis treatment was performed in a manner similar to Example 3, except that the TMS-derivatization pretreatment (methoxim derivatization treatment) step was eliminated, to obtain 1 mL of a test sample solution. 25 μL of the test sample solution was subjected to mass spectrometric analysis in a manner similar to Example 1. Analytical result is shown in FIG. 14.

As obvious from FIGS. 13 and 14, this system gave peaks of chain-structured fructose isomers more when the TMS-derivatization pretreatment (methoxim derivatization treatment) step (FIG. 13) is performed than when the TMS-derivatization pretreatment is not performed (FIG. 14) (see peaks in the range indicated by reference sign X in FIGS. 13 and 14). Regarding sucrose, the number of the peaks of multiple isomers generated in the case when the TMS-derivatization pretreatment is performed is decreased to the number of the peaks of particular isomers (see peaks in the range indicated by reference sign Y in FIGS. 13 and 14). The results show that it is possible by the TMS-derivatization pretreatment to generate particular isomers (trimethylsilylated organic compounds) of organic compounds preferentially among multiple isomer during trimethylsilylation.

REFERENCE SIGNS LIST 1,2 pre-analysis treatment device
E ion-exchange unit
D derivatization unit
F trimethylsilylation pretreatment unit
S solid-phase cartridge
B1, B2 cleaning solvent-storing unit
B3 dehydration solvent-storing unit
B4 waste liquid-storing unit
B5 sample-storing unit
B6 analysis solution-storing unit
B7 derivatization reagent-storing unit
B8, B9 push-out solvent-storing unit
B10 pretreatment reagent-storing unit
P1, P2 cleaning solvent feed pump
P3 first feed pump
P8 second feed pump
P9 third feed pump
V switching valve
v1, v2, v3 valve
N1 first feed nozzle
N2 second feed nozzle
N4 third feed nozzle e1 outlet side of first feed nozzle
e2 outlet side of second feed nozzle
e3 inlet side of solid-phase cartridge
e4 outlet side of third feed nozzle
A cartridge-holding means
C container-storing means
L1, L2, L3, L4, L8, L9 channel

The invention claimed is:

1. A pre-analysis treatment device usable for an amino acid, organic acid, and glucide, the pre-analysis treatment device comprising
    a sample-storing unit for storing a test sample,
    a solid-phase cartridge having a strong ion-exchange resin phase that adsorbs at least one organic compound selected from amino acids, organic acids and glucides possibly contained in the test sample,
    a dehydration solvent-storing unit for storing a dehydration solvent that dehydrates the strong ion-exchange resin phase on which the test sample is loaded,
    a first nozzle used for at least one of discharging the dehydration solvent, withdrawing the test sample, and ejecting the test sample,
    a first feed pump for supplying the dehydration solvent and the test sample via the first nozzle to the solid-phase cartridge,
    a derivatization reagent-storing unit for storing a derivatization reagent that trimethylsilylates the organic compound adsorbed on the strong ion-exchange resin phase,
    a push-out solvent-storing unit for storing a non-ion-exchanging push-out solvent that pushes the trimethylsilylated organic compound out of the solid-phase cartridge,
    a second nozzle used for at least one of discharging the elution solvent, withdrawing the derivatization reagent, and discharging the derivatization reagent,
    a second feed pump for supplying the derivatization reagent and the elution solvent via the second nozzle to the solid-phase cartridge,
    an ion-exchange unit configured to (i) withdraw a prescribed amount of the test sample by the first feed pump in a state that an outlet side of the first nozzle is connected to the sample-storing unit, (ii) then feed the test sample withdrawn, with the dehydration solvent in a state that the outlet side of the first nozzle is connected to an inlet side of the solid-phase cartridge, (iii) load the test sample on the solid-phase cartridge to allow the strong ion-exchange resin phase to adsorb the organic compound, and (iv) then supply the dehydration solvent to dehydrate the strong ion-exchange resin phase, and
    a derivatization unit configured to (i) withdraw a prescribed amount of derivatization reagent by the second feed pump in a state that an outlet side of the second nozzle is connected to the derivatization reagent-storing unit, (ii) feed the prescribed amount of the derivatization reagent with the elution solvent in a state that the outlet side of the second nozzle is connected to an inlet side of the solid-phase cartridge, (iii) suspend the feed of the elution solvent for a particular time so as to retain the derivatization reagent, thereby trimethylsilylating the organic compound adsorbed on the strong ion-exchange resin phase in the ion-exchange unit, and simultaneously desorbing the trimethylsilylated organic compound from the strong ion-exchange resin phase, and (iv) then supply the push-out solvent to push the desorbed trimethylsilylated organic compound out of the solid-phase cartridge.

2. The pre-analysis treatment device usable for an amino acid, organic acid, and glucide according to claim 1, further comprising
    a pretreatment reagent-storing unit for storing a trimethylsilylation pretreatment reagent for generating a particular isomer of an organic compound preferentially among multiple isomers possibly generated during trimethylsilylation,
    a third nozzle for withdrawing or ejecting the trimethylsilylation pretreatment reagent,
    a third pump for supplying the trimethylsilylation pretreatment reagent via the third nozzle to the solid-phase cartridge, and
    a trimethylsilylation pretreatment unit configured to (i) withdraw a prescribed amount of the trimethylsilylation pretreatment reagent by the third feed pump in a state that the outlet side of the third nozzle is connected to the pretreatment reagent-storing unit, (ii) feed the prescribed amount of the trimethylsilylation pretreatment reagent in a state that the outlet side of the third nozzle is connected to the inlet side of the solid-phase cartridge, and (iii) suspend the feed of the trimethylsilylation pretreatment reagent for a particular time, thereby retaining the trimethylsilylation pretreatment reagent, and (iv) pretreat the organic compounds adsorbed on the strong ion-exchange resin phase in the ion-exchange unit with the trimethylsilylation pretreatment reagent.

3. The pre-analysis treatment device usable for an amino acid, organic acid, and glucide according to claim 1, wherein the ion-exchange unit is configured to supply the dehydration solvent to the solid-phase cartridge through the outlet side of the first nozzle connected to the inlet side of the solid-phase cartridge, before loading the test sample on the solid-phase cartridge.

4. The pre-analysis treatment device usable for an amino acid, organic acid, and glucide according to claim 1, further comprising
    at least one cleaning solvent-storing unit for storing a cleaning solvent for cleaning the solid-phase cartridge,
    at least one cleaning solvent feed pump for supply of the cleaning solvent from the cleaning solvent-storing unit via the first nozzle to the solid-phase cartridge, and
    a switching valve for switching a channel having the first feed pump and a channel having the cleaning solvent feed pump, thereby allowing one of the channels to be communicable with the first nozzle,
    wherein the ion-exchange unit is configured to supply the cleaning solvent to the solid-phase cartridge through the outlet side of the first nozzle connected to the inlet side of the solid-phase cartridge, before the test sample is loaded on the solid-phase cartridge.

5. The pre-analysis treatment device usable for an amino acid, organic acid, and glucide according to claim 1, wherein the derivatization unit is configured to complete withdrawal of the elution solvent, before withdrawing the derivatization reagent by the second feed pump.

6. The pre-analysis treatment device usable for an amino acid, organic acid, and glucide according to claim 1, wherein the derivatization reagent contains at least one compound selected from N-methyl-N-trimethylsilyltrifluoroacetamide (MSTFA), N,O-bis(trimethylsilyl)trifluoroacetamide (BSTFA), and trimethylchlorosilane (TMCS).

7. The pre-analysis treatment device usable for an amino acid, organic acid, and glucide according to claim 6, wherein the derivatization reagent contains pyridine.

8. The pre-analysis treatment device usable for an amino acid, organic acid, and glucide according to claim 1, wherein the elution solvent is at least one of hexane and a mixed solution of acetone and hexane.

9. The pre-analysis treatment device usable for an amino acid, organic acid, and glucide according to claim 1, wherein the strong ion-exchange resin phase comprises at least one resin selected from strong cation-exchange resins, strong anion-exchange resins, and a combination of a strong cation-exchange resin and a strong anion-exchange resin.

10. The pre-analysis treatment device usable for an amino acid, organic acid, and glucide according to claim 1, wherein the prescribed amount of the derivatization reagent supplied is 0.07 to 2.2 times larger than an apparent volume of the strong ion-exchange resin phase.

11. An pre-analysis treatment method of pretreating amino acid, organic acid, and glucide, the method comprising loading a test sample on a solid-phase cartridge containing a strong ion-exchange resin phase that adsorbs at least one organic compound selected from amino acids, organic acids, and glucide, thereby allowing the strong ion-exchange resin phase to adsorb the organic compound, supplying a dehydration solvent to the solid-phase cartridge on which the test sample is loaded, thereby allowing the strong ion-exchange resin phase to be dehydrated, supplying a prescribed amount of a derivatization reagent to the strong ion-exchange resin phase which the test sample is loaded on and is subsequently dehydrated, and retaining the resulting strong ion-exchange resin phase for a particular time, thereby trimethylsilylating the organic compound adsorbed on the strong ion-exchange resin phase, and simultaneously desorbing the trimethylsilylated organic compound from the strong ion-exchange resin phase, and supplying a non-ion-exchanging push-out solvent to the solid-phase cartridge where the derivatization reagent is retained, to push the desorbed trimethylsilylated organic compound out of the solid-phase cartridge.

12. The pre-analysis treatment method for pretreating amino acid, organic acid, and glucide according to claim 11, further comprising supplying a prescribed amount of trimethylsilylation pretreatment reagent to the strong ion-exchange resin phase which the test sample is loaded on and is subsequently dehydrated, and retaining the resulting strong ion-exchange resin phase for a particular time, thereby generating a particular isomer of an organic compound adsorbed on the strong ion-exchange resin phase preferentially among multiple isomers possibly generated during trimethylsilylation.

* * * * *